US006239048B1

(12) United States Patent
Wilson et al.

(10) Patent No.: US 6,239,048 B1
(45) Date of Patent: May 29, 2001

(54) LIGHT-ACTIVATED ANTIMICROBIAL AND ANTIVIRAL MATERIALS

(75) Inventors: John E. Wilson, Quakertown, PA (US); Christopher Bull, Bethesda, MD (US)

(73) Assignee: FiberMark, Inc., Brattleboro, VT (US)

( * ) Notice: Subject to any disclaimer, the term of this patent is extended or adjusted under 35 U.S.C. 154(b) by 0 days.

(21) Appl. No.: 08/365,464

(22) Filed: Dec. 28, 1994

(51) Int. Cl.$^7$ ..................................................... B32B 27/04
(52) U.S. Cl. ........................ 442/123; 442/153; 428/913
(58) Field of Search ........................................ 428/245, 261, 428/262, 264, 265, 286, 288, 289, 290, 913; 442/123, 153

(56) References Cited

U.S. PATENT DOCUMENTS

| | | | |
|---|---|---|---|
| D. 333,404 | 2/1993 | Thompson | D6/602 |
| 3,310,459 | 3/1967 | Guthrie et al. | 162/12 |
| 3,317,376 | 5/1967 | Schattner | 167/38.7 |
| 3,794,736 | 2/1974 | Abbott et al. | 424/78 |
| 3,817,739 | 6/1974 | Abbott et al. | 71/67 |
| 3,828,731 | 8/1974 | White | 119/1 |
| 3,860,709 | 1/1975 | Abbott et al. | 424/184 |
| 3,865,728 | 2/1975 | Abbott et al. | 210/169.71 |
| 3,876,459 | 4/1975 | Burrill | 117/141 |
| 3,926,896 | 12/1975 | Dumoulin | 260/31.2 R |
| 3,962,500 | 6/1976 | Smith | 427/387 |
| 3,987,797 * | 10/1976 | Stephenson | 606/231 |
| 4,009,313 * | 2/1977 | Crawford et al. | 428/290 |
| 4,143,088 | 3/1979 | Favre et al. | 260/825 |
| 4,151,327 | 4/1979 | Lawton | 428/447 |
| 4,259,103 | 3/1981 | Malek et al. | 71/67 |
| 4,311,479 | 1/1982 | Fenn et al. | 8/495 |
| 4,381,380 | 4/1983 | LeVeen et al. | 525/452 |
| 4,395,454 | 7/1983 | Baldwin | 428/290 |
| 4,401,712 | 8/1983 | Morrison | 428/289 |
| 4,406,892 | 9/1983 | Eudy | 424/184 |
| 4,408,996 | 10/1983 | Baldwin | . |
| 4,411,928 | 10/1983 | Baldwin | 427/2 |
| 4,414,268 | 11/1983 | Baldwin | 428/289 |
| 4,421,826 | 12/1983 | Ohlson et al. | 428/394 |
| 4,425,372 | 1/1984 | Baldwin | 427/2 |
| 4,448,810 | 5/1984 | Westall | 427/302 |
| 4,460,369 | 7/1984 | Seymour | 604/897 |
| 4,467,013 | 8/1984 | Baldwin | 428/289 |
| 4,525,565 | 6/1985 | Laisney et al. | 528/17 |
| 4,525,566 | 6/1985 | Homan et al. | 528/17 |
| 4,529,749 | 7/1985 | Favre et al. | 523/122 |
| 4,631,297 | 12/1986 | Battice et al. | 521/78 |
| 4,643,181 | 2/1987 | Brown | 128/156 |
| 4,721,511 | 1/1988 | Kupits | 8/188 |
| 4,822,667 | 4/1989 | Goad et al. | 428/265 |
| 4,847,089 | 7/1989 | Kramer et al. | 424/405 |
| 4,889,765 | 12/1989 | Wallace | 428/290 |
| 5,069,907 | 12/1991 | Mixon et al. | 424/445 |
| 5,073,295 | 12/1991 | Bruttel et al. | 252/301.19 |
| 5,079,004 | 1/1992 | Blank et al. | 424/404 |
| 5,087,499 | 2/1992 | Sullivan | 428/85 |
| 5,103,816 | 4/1992 | Kirschbaum et al. | 128/207 |
| 5,177,128 | 1/1993 | Lindemann et al. | 524/44 |
| 5,180,585 | 1/1993 | Jacobson et al. | 424/405 |
| 5,190,810 | 3/1993 | Kurschbaum et al. | 428/246 |
| 5,197,493 | 3/1993 | Grier-Idris | 128/853 |
| 5,212,011 | 5/1993 | Ishikawa et al. | 428/343 |
| 5,215,816 | 6/1993 | Shibata et al. | 428/266 |
| 5,217,493 | 6/1993 | Raad et al. | 623/11 |
| 5,222,507 | 6/1993 | Taylor | 128/849 |
| 5,252,103 | 10/1993 | Kamata et al. | 8/554 |
| 5,271,998 | 12/1993 | Duckett | 428/251 |
| 5,281,662 * | 1/1994 | Ito et al. | 525/54.1 |

FOREIGN PATENT DOCUMENTS

| | | |
|---|---|---|
| 0136900 | 4/1985 | (EP) . |
| 0505775 | 9/1992 | (EP) . |
| 9216681 | 10/1992 | (WO) . |

OTHER PUBLICATIONS

1979 National Technical Conference Book of Paper for the American Association of Textile Chemists and Colorists: Richard L. Gettings and B. Triplett; "A New Durable Antimicrobial Finish for Textiles" pp. 259–262.

Arch Ophthalmol; vol. 105, Oct. 1987; Laboratory Sciences; Melvin Roat, et al.; "The Antiviral Effects of Rose Bengal and Fluorescein"; pp. 1415–1417.

Science, vol. 188, Apr. 4, 1975; "Butylated Hydroxytoluene Inactivates Lipid–Containing Viruses"; pp. 64–66.

J.Am.Chem.Soc., vol. 115, No. 6, 1993; Kensuke Naka, et al.; "Molecular Harpoons. Membrane–Disruptive Surfactants that Can Recoganize Osmotic Stress in Phospholipid Bilayers" pp. 2278–2286.

Proc. Natl. Acad.Sci.USA, vol. 87, pp. 2980–2984, Apr. 1990; Applied Biological Sciences; S. Devanathan, et al.; "Readily available fluorescein isothiocyanate–conjugated antibodies can be easily converted into targeted phototoxic agents for antibacterial, antiviral, and anticancer therapy".

Proc. Natl. Acad.Sci.USA,vol. 90, pp. 158–162, Jan. 1993; Medical Sciences; John Lenard, et al.; "Photodynamic inactivation of infectivity of human immunodeficiency virus and other enveloped viruses using hypericin and rose bengal: Inhibition of fusion and syncytia formation".

(List continued on next page.)

Primary Examiner—Terrel Morris
Assistant Examiner—Ula C. Ruddock
(74) Attorney, Agent, or Firm—Elman & Associates

(57) ABSTRACT

A substrate such as a woven or nonwoven fabric bound with a light-activated dye alone or in combination with additional conventional antimicrobial agents. The substrate is impregnated with a light-activated non-leachable dye having antimicrobial and/or antiviral characteristics which can be imparted to the substrate. The dye is bound by a cationic or anionic binder such as a water soluble polymer or carrageenan. Upon exposure to normal light, the dye generates singlet oxygen that kills microorganisms and viruses.

12 Claims, 1 Drawing Sheet

OTHER PUBLICATIONS

Photochemistry and Photobiology, vol. 28, pp. 325–329; S.A. Bezman, et al.; "Photodynamic Inactivation of E.Coli by Rose Bengal Immodiblized on polystyrene beads", No Date Given.

Water Res. vol. 19, No. 12, pp. 1465–1469, 1985; A. Savino, et al.; "Photodynamic Inactivation of E.Coli by immodibilized or coated dyes on insoluble supports".

ASTM Designation: D1117–80 "Standard Methods of Testing Nonwoven Fabrics" pp. 304–308, No Date Given.

ASTM Designation: D 1424–83 "Standard Test methods for Tear Resistant of Woven Fabrics by Falling–Pendulum (Elmendorf) Apparatus"; pp. 379–384, No Date Given.

ASTM Designation: D 1682–64 (Reapproved 1975) "Standard TEst Methods for Breaking Load and Elongation of Testible Fabrics" pp. 457–462, No Date Given.

ASTM Designation: D 1230–85 "Standard Test Method for Flammability of Apparel Textiles"; pp. 310,314, No Date Given.

ASTM Designation: D202–82 "Standard Test Methods of Sampling and Testing Untreated paper used for electrical insulation" pp. 16, 29 and 56, No Date Given.

AATCC Technical Manual/1986; AATCC Test Method 8–1985; "Colorfastness to Crocking: AATCC Crockmeter Method" pp. 21–22.

DuPont "Versatile TYZOR Organic Titanates" pp. 1–28, No Date Given.

TAPPI Press "Nonwovens Primer" pp. 1–29, No Date Given.

D.R. Battice and M.G. Hales; Dow Corning Corporation "A New Technology For Producing Stabilied Foams Having Antimicrobial Activity" pp. 108–112, No Date Given.

DOW Corning "Information about Antimicrobial Agents" (Dow Corning 5701 Antimicrobial Agent for Stabilized Foams) 4–Pages, No Date Given.

DOW Corning "Information about Antimicrobial Agents" (Dow Corning 5700 Antimicrobial Agent) 4–Pages, No Date Given.

Color Chemistry: Syntheses, Properties and Applications of Organic Dyes and Pigments, Second, revised edition, 1991, Heinrich Zollinger, New York, VCH Publishers, Inc. pp. 267–291, 301–319, 416–420.

Nonwovens Industry, Oct. 1991; J.McDowell, PhD, "Better Medicine Trhough Nonwovens Nonwoven Applications In medical Textiles", pp. 21–22, 24, 26, 28.

Archives of Biochemistry and Biophysics, vol. 256, No. 1, Jul. 1987; J.Martin et al. "Oxygen Radicals Are Generated by Dye–Mediated intercellular Photooxidations: A Role for Superoxide in Photodynamic Effects," pp. 39–49.

J. Environ. Sci. Health, A23(2), 1988; Dean F. Martin; "Photoinactivation of Three Viruses by Rose Bengal," pp. 127–137.

J. of Photochemistry and Photobiology, B: Biology, vol. 4, 1989; Thomas A. Dahl, Oscar Baldes–Aguilera, W.Midden and D.C. Neckers; "Partition of Rose Bengal Anion from Aqueous Medium into a Lipophilic Environment in the Cell Envelope of *Salmonella typhimurium*: Implications for Cell–Type Targeting in Photodynamic Therapy" pp. 171–184.

J. Antibact. Antifung. Agents, vol. 6, No. 9, 1978; Yoshio Sakagami, et al. The Biological Effect of Pigments Against Microorganisms: The Screening Method for the pigments which were showing the activity of cytoplasmic biosynthesis inhibitors against bacteria, pp. 1–8.

Immunopharmacology and Immunotoxicology, vol. 14(4), 1992; Robert W. Buckheit, Jr., E. Lucile White, William M. Shannon, A. Guerrero, J.P. Pivel, L. Carrasco, J.A. Leal and and Michael A. Chirigos; "Significant Anti–HIV Activity of New Modified Polyanionic Poymers in Vitro," pp. 707–721.

Photochemistry and Photobiology, vol. 59, No. 5, 1994; Kathleen G. Specht; "The Role of DNA Damage in PM2 Viral Inactivation by Methylene Blue Photosensitization," pp. 506–514.

Arch Ophthalmol, vol. 105, Oct.1987; Melvin I. Roat, MD, et al.; "The Antiviral Effects of Rose Bengal and Fluorescein." pp. 1215–1417.

Wilcock, Anne Elizabeth L., Ph.D; dissertation "The Antimicrobial Activity of Selected Cationic and Fiber Reactive Dyestuffs," Purdue University, 1977.

Singlet $O_2$; vol. 1, Physical–Chemical Aspects; pp. 10, 18–19, 59, 189; vol. IV, Polymers and Biomolecules; pp. 36–50,63–65; Editor; Aryeh A. Frimer, PhD; CRC Press, inc., Boca Raton,FL 1985.

"Virus Inactivation of Plasma by Methylene Blue Photoactivation: Approaches, Toxicology, Virology and Plasma Protein Quality," pepr presented by John Chapman (Baxter Healthcare) at the Viral Blood Safety & Screening conference; Oct. 17–19, 1994; Washington, D.C.

"Inactivation of Blood–Borne Viruses: Rational Design of Photoactivation Sensitizers," paper presented by Dr. Raymond P. Goodrich, No Date Given.

Proc. Natl. Acad. Sci., vol. 91, Jun. 1994, Raymond P. Goodrich, et al., "Selective Inactivation of Viruses in the Presence of Human Platelets; UV Sensitization with Psoralen Derivatives," pp. 5552–5556.

Photochemistry and Photobiology, vol. 58, No. 1, 1993, Saroj Rai, et al., "Tramatic Improvements in Viral Inactivation with Brominated Psoralens, Naphthalenes and Anthracenes," pp. 59–65.

"Hypericin–Based Viral Inactivation," Presentation by Dr. Alfonso Tobia, No Data Given.

"Photodynamic Decontamination of Blood for Tranfusion," paper presented by Dr. Ehud Ben–Hur, No Date Given.

Photochemistry and Photobiology, vol. 60, No. 2,1994, S. Rywkin, et al., New Phthalocyanines for Photodynamic Virus Inactivation in Red Blood Cell Concentrates, pp. 165–170.

"Use of Photochemical Products for Viral Eradication in Banked Blood," presentation by Dr. Tran C. Chan, No Date Given.

"Removal/Inactivation of Intracellular and Extracellular HIV Contaminants in Human Plasma with Filtration and Methylene Blue Treatment," poster presentation by Chong Sun, Ph.D., No Date Given.

\* cited by examiner

LIGHT-ACTIVATED ANTIMICROBIAL AND ANTIVIRAL MATERIALS

BACKGROUND OF THE INVENTION

Non-woven fabrics are used in the manufacture of products such as washing and wiping cloths, diapers, sanitary napkin covers, hospital gowns, surgical drapes, sheets, pillow cases, curtains, backing material for garments, table cloths, bed spreads, sponges, underpads, etc. For these products and products such as sheets, pillow cases, hospital gowns and surgical drapes in particular, it is highly desirable to render the non-woven textiles or other non-woven type materials antimicrobial and/or antiviral. Indeed, the passage of liquid through surgical drapes, which are used during surgical procedures to isolate the patient from the operating room personnel and environment, is one source of bacterial contamination to the patient.

Similarly, rendering woven fabrics and fleece antimicrobial or antiviral is also advantageous.

Conventionally, harsh chemicals are required to provide antimicrobial effects. For example, a normal disinfectant solution of 0.15% to 2% glutaraldehyde is required to kill microorganisms and viruses on surfaces being cleaned, and the exposure time required is from 3 to 18 hours. Glutaraldehyde is corrosive, is a sensitizer and harmful if inhaled, absorbed through the skin or swallowed. Indeed, the OSHA personal exposure limit to glutaraldehyde is 0.2 ppm. Similarly, although chlorinated water disinfecting solutions such as sodium hypochlorite and chlorinated $H_2O$ kill most microorganisms and some viruses including HIV in seconds to minutes, depending upon the concentration, the activity of chlorinated water is reduced by organic material and some metallic catalysts. Hydrogen peroxide solutions kill, but have no long term effect; they are quickly inactivated by organic materials with which they react. Iodine in high concentration in solution will kill most microorganisms and some viruses, however, it has an irritating odor and residue except with Iodophors. Alcohols are the most effective and frequently used agents for sterilization and disinfection, but are flammable in concentrations required for effectiveness. Phenols are frequently used with halogens and detergents as a general disinfectant for toilets, stables, cesspools, floors, drains, and other surfaces, but they are harmful to tissues in high concentration and they have a disagreeable odor. Detergents in combination with quaternary ammonium compounds are widely used to kill bacteria in hospitals, restaurants, and in food processing plants, however, they may not kill some viruses and their effectiveness is reduced by hard water and fibrous materials. Heavy metals are used to kill some bacteria and viruses, but they are ineffective against tuberculosis and are inactivated by organic compounds. Although boiling kills microorganisms, it is not practical for many objects that must remain dry or cannot handle the high temperature for the 15 to 20 minutes required to kill microorganisms.

Light-activated dyes are known to exhibit antimicrobial activity in water. However, they are not necessarily effective in the dry state or when bound in a polymeric system. For surgical drape applications in particular, the cellulosic material and other additives necessary for a fenestration place demands on the binder. A satisfactory product must have a dye bound to a cellulosic non-woven material lightly enough to be effective, yet tightly enough to avoid excessive leaching. More specifically, the light-activated dye must be incorporated into the substrate such that it retains its light-activatable property yet does not leach significantly therefrom.

The prior art includes disclosures of nonwoven materials rendered antimicrobial. For example, European Patent Application 0 136 900 discloses a nonwoven fabric having antimicrobial properties suitable for use as a surgical drape. The surgical drape is made with a cellulose-containing, nonwoven fabric that is bonded with a binding agent which contains little or no anionic surfactant or is made with a nonionic surfactant, such as a copolymer of ethylene and vinyl acetate, and polyhexamethylene biguanide salt as the antimicrobial.

Similarly, U.S. Pat. No. 5,069,907 discloses a surgical drape comprising a synthetic polymeric film such as polyethylene or polyurethane, and an antimicrobial agent such as 5-chloro-2-(2,4-dichlorophenoxy)phenol incorporated throughout the film. Also disclosed are surgical drapes comprising fabric forming material to which the antimicrobial agent is directly added prior to forming the material into a drape.

U.S. Pat. No. 4,643,181 discloses surgical dressings and incise drapes having an adhesive surface, the adhesive containing a salt of polyhexamethylene biguanide as an antimicrobial agent.

U.S. Pat. No. 4,721,511 discloses a leach resistant antimicrobial fabric, wherein the antimicrobial agent is a silane quaternary amine such as 3-(trimethoxysilyl)-propyloctadecyl-dimethyl ammonium chloride.

However, the prior art does not disclose a substrate having bound to it a light-activatable dye to obtain antimicrobial and/or antiviral effects. It is therefore an object of this invention to provide such a substrate.

SUMMARY OF THE INVENTION

The problems of the prior art have been overcome by the present invention, which provides a substrate bound with a light-activated dye alone or in combination with additional conventional antimicrobial and/or antiviral agents. The substrate includes woven and nonwoven fabrics that are then impregnated with a light-activated non-leachable dye having antimicrobial and/or antiviral characteristics which can be imparted to the substrate. The dye is bound to the substrate by a cationic or anionic water soluble polymer. Upon exposure to normal light, the dyes used in the present invention generate singlet oxygen that kills microorganisms and viruses.

DETAILED DESCRIPTION OF THE INVENTION

Figure 1:
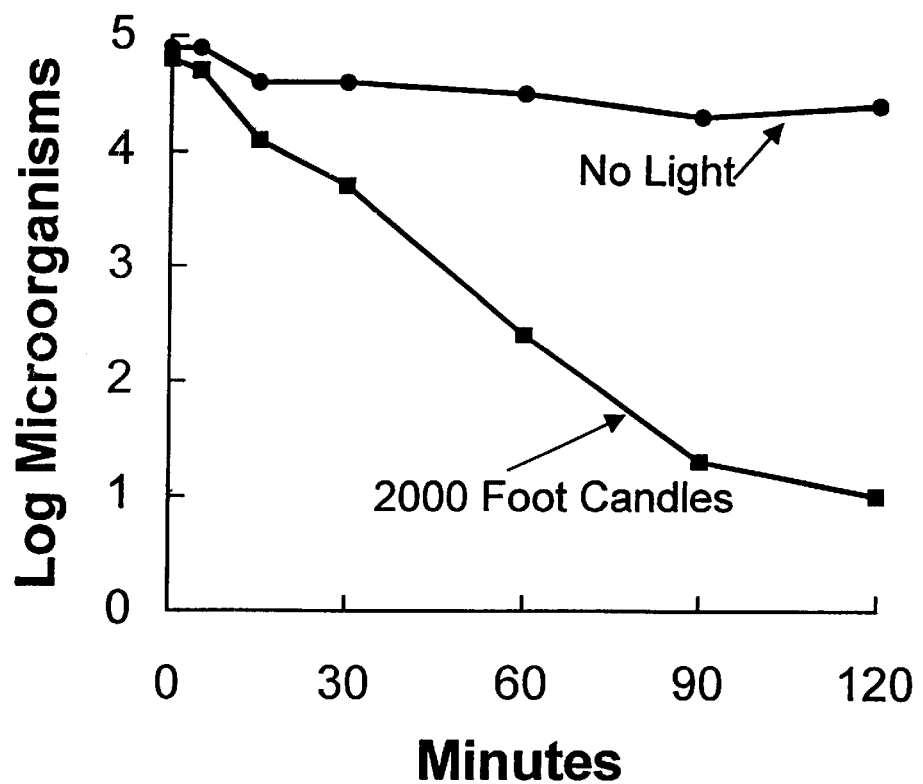
FIG. 1 is a graph showing the antimicrobial activity of a non-woven fabric impregnated with Rose Bengal in accordance with the present invention.

The preferred substrates for use in the present invention are non-woven fabrics which utilize as the fibrous base such fibers as polyester, polyethylene, polypropylene, rayon, acrylics, blends of these synthetics or blends of these synthetics with natural fibers such as cellulose. Preferably the fabric contains some amount of cellulosic fiber, either in the form of regenerated cellulose such as rayon, cotton fibers or woodpulp fibers. One suitable material is an airlaid fabric manufactured by WALKISOFT USA and known as WALKISOFT grade FG400WR, which is composed of non-elemental chlorine bleached virgin wood pulp fibers bonded with a latex binder which comprises approximately 24.5% of the total weight of the substrate. In the preferred embodiment of the invention, the substrate is a non-woven fenistration material that is conventionally applied to a patient surrounding the portion of the body where a surgical incision is to be made.

Other suitable substrates include woven fabrics, paper, film and fleece.

Suitable dyes for use in the present invention can be categorized into two groups, namely, anionic dyes and cationic dyes. Although the present inventors should not be limited thereto, they believe that certain dyes within these groups exhibit light-activatable antimicrobial and/or antiviral activity by a mechanism which involves interaction with and transferring energy to oxygen so as to provide a source of an active or excited oxygen species known as singlet oxygen. Singlet oxygen is an activated form of the usual triplet state molecular oxygen. It is much more reactive with organic molecules than is triplet oxygen, since the singlet spin state matches that of the organic substances. It is sufficiently stable in water (half life of several microseconds) that it can diffuse somewhat from its point of origin. It is known to be bacteriocidal. Anionic dyes that are capable of providing a source of singlet oxygen in accordance with the present invention include fluorescein derivatives, preferably the alkali metal salts of Rose Bengal, 4,5,6,7-tetrachloro-2',5',7'-tetraiodo fluorescein sodium or potassium -(hereinafter, reference to Rose Bengal means an alkali metal salt thereof). Suitable cationic dyes include 3-amino-7-(dimethylamino)-2-methylphenothiazin-5-ium chloride (also known as Tolonium chloride or Toluidine Blue O), Thionin and Methylene Blue. The dyes may be used alone or in combination. The dyes are used in an antimicrobial and/or antiviral effective amount, and are generally effective at very low levels, such as concentrations as low as 0.1 micromolar. In general, dye concentrations on the order of 1–100 micromolar, preferably 1–50 micromolar, are desirable to provide the desired rapidity of viral decontamination without leaving unwanted quantities of residual dye on the treated material. Some dyes exhibit antiviral activity at concentrations less than 1 micromolar and ambient light, that is significantly less than 200 foot candles. Where rapid destruction of viral contamination (at least four powers of ten reduction) is desired, it is preferable to use dye concentrations on the order of 1–50 micromolar in conjunction with light intensity on the order of 1,000 to 2,000 or more foot candles at the surface of the aqueous solution containing the dye. (For surgical drape applications, surgical field lighting is generally in the range of about 2000 foot candles).

One or more of the foregoing dyes is effective against one or more of the following bacteria: *Escherichia coli, Pseudomonas aeroginosa, Enterobacter cloacae, Staphylococcus aureus, Enterococcus faecalis, Klebsiella pneumoniae, Salmonella typhimurium, Staphylococcus epidermidis, Serratia marcescens, Mycobacterium bovis* (TB), methicillin resistant *Staphylococcus aureus* and *Proteus vulgaris.*

In addition, the foregoing dyes are effective against viruses, particularly enveloped viruses, such as Herpes, HIV, and viruses associated with the common cold.

Suitable binders for use in the present invention include cationic and anionic water soluble polymers. Preferably, a cationic binder is used with an anionic dye, and an anionic binder is used with a cationic dye. A preferred cationic binder is a prepolymer derived from a polyether based hydrophilic polyurethane, available commercially from Hampshire Chemical Corp. as "DARATHANE® WB-4000". DARATHANEO WB-4000 is disclosed in U.S. Pat. No. 4,421,826 (the disclosure of which is herein incorporated by reference), and is a water solution (dispersion) of a blocked polyurethane prepolymer that forms a tough continuous film on curing that has excellent gloss and is resistant to attack by organic solvents. The films are hydrophilic and retains a cationic charge. The polyurethane is chain extended to facilitate curing and impart a cationic charge to the molecule, and is further treated to stabilize it and impart water dispersibility. Other suitable binders for anionic dyes include cationic resins, such as polyquaternary amine chloride (sold commercially as NALKAT 7607 by Nalco Chemical), cationic polyamine sold commercially as CYPRO 516 by Cytec Industry, and cationic polyelectrolyte sold commercially as PERCOL 402 by Allied Colloid. Suitable anionic binders for cationic dyes include carrageenan, which is a hydrocolloid extracted from red seaweed (available commercially from FMC under the trademark Viscarin®), sodium alginate and sodium carboxymethylcellulose.

Preferably the dye to binder ratio ranges from about 0.008 to about 0.016 solids on solids. Ratios higher than about 0.016 tend to result in dye leaching. Too little dye results in poor antimicrobial and/or antiviral kill. The lowest level of Rose Bengal dye treatment on a nonwoven to give high percent kill rates is 0.0012% solids on solids. Toluidine Blue O is very active in killing bacteria at 0.002% under both surgical illumination (2000 fc) and room lighting (200 fc). The particular dye to binder ratio used may also depend upon other factors, such as the presence of a wetting agent.

The choice of which dye to use will depend upon the particular application. For example, Toluidine Blue O is much more effective in killing *Klebsiella pneumoniae* and Methicillin Resistant *Staphylococcus aureus* than is Rose Bengal. Also, Rose Bengal is not as effective in the presence of blood, apparently since blood absorbs light in the region of the visible spectrum where Rose Bengal absorbs light. Methylene Blue has a better kill rate against various viruses in the presence of blood than does Toluidine Blue O and Thionin, apparently because less of the light that excites Methylene Blue is absorbed by blood than for the other dyes.

The choice of which binder to use will depend on the particular application, as well as the dye chosen. For example, carrageenan, an anionic polysaccharide hydrocolloid extracted from red seaweed, is a better hydrophilic binder for Toluidine Blue O than the cationic WB4000 polymer. However, Rose Bengal is not bound by carrageenan, since both are anionic.

Other ingredients can be added, as long as they are not deleterious to the antimicrobial and/or antiviral activity of the dye. For example, a wetting agent such as Lexaine C or Mazeen C-15 can be bound with the binder to enhance the activity of Toluidine Blue O against *Klebsiella pneumoniae.*

The antimicrobial and antiviral substrates of the invention can be prepared by placing the substrates in a treatment solution containing the antimicrobial or antiviral agent and the binder. The treatment solution is prepared by mixing a suitable amount of the dye with water, to which a binder solution is added. The material to be treated is then placed in a shallow bath of the treatment solution until it is thoroughly wet (about 5 to 15 seconds or less). The saturated material is then removed from the bath and passed between two squeeze rollers (usually chrome plated steel rolls) having a squeeze roll gap or nip of 0.005 to 0.006 inches. The rollers are turned by hand with a hand crank so that when a shorter edge of the thoroughly soaked material is placed on the bottom roller, the material is pulled between the nip made by the two rolls. The action of the nip on the material squeezes out excess treatment solution leaving about 150% to 160% of the original weight of the material as treatment solution on the material. (This is normally referred to as 150% to 160% wet add on. The amount of wet add on (%) is determined by subtracting the dry weight of the material before it is treated from the wet weight of the material after it is passed through the squeeze rolls, and dividing the result by the original dry weight and multiplying by 100.) If the wet add on is not within the desired range for the treatment, the sample is discarded. The squeeze roll gap can be adjusted smaller or larger to obtain lesser or greater amounts of treatment add on. After the right amount of wet add on is achieved, the wet sample is placed in a forced hot air oven for 90 seconds at 300° F. to dry. After removal from the oven the sample is ready for testing, which may require conditioning at 50% relative humidity and 72° F. for four (4) hours.

Those skilled in the art will appreciate that the amount of light exposure effective for causing the antimicrobial and antiviral effects of the present invention will depend upon the particular bacteria or virus involved, and the amount of desired kill. Normal room light, such as fluorescent cool light (approximately 150–200 foot candles) is generally sufficient. Bacteria and viruses more sensitive to the singlet oxygen generated by the light-activated dye require less light. Typical surgical room illumination of about 2000 foot candles is more than sufficient.

Turning now to FIG. 1, hand sheets of Merfin 60850 non-woven at 85 grams per square meter were saturated at 150% wet pickup with the following formula: deionized water 316 grams, DATATHANE® WB4000 binder 4 grams, and Rose Bengal 0.01 grams. After saturating with this formula, the wet hand sheets were dried for 90 seconds at 300° F. in an air circulating laboratory oven. Test swatches of this treated non-woven were tested for microbiological kill by inoculating the swatches with a known concentration of *Staphylococcus aureus* bacteria and then exposing the swatches to light (2000 foot candles) or dark for given periods of time. After exposure for the required time, the number of live bacteria remaining on the test swatches was determined. The log of the remaining live bacteria versus the exposure time to light (2000 foot candles) or dark (no light) is plotted in FIG. 1. It is clear from this graph that the test swatches of the non-woven treated with Rose Bengal show significant reductions in the *Staphylococcus aureus* bacteria when exposed to light of 2000 foot candle intensity. The longer the exposure to light, the fewer live bacteria recovered from the test swatches. In the absence of light, essentially all of the bacteria are recovered from the test swatches.

In the Examples that follow, the following test protocol was used unless otherwise specified.

All microbial strains were obtained from American Type Culture Collection (ATCC) in Rockville, Md. A seed culture was grown up, diluted appropriately, and used to inoculate six swatches of each material to be tested. Two of the swatches were immediately run through the recovery procedures to serve as zero time controls. Two more swatches were kept in the dark, while the last two swatches were illuminated for the specified times, following which all four were run through the recovery procedure. After a suitable incubation, bacterial colonies were counted, and log reduction and percent kill calculated.

For inoculum preparation, the test organism was transferred into 50 ml of sterile tryptic soy broth in a 250 ml baffled Erlenmeyer flask and incubated at 30° C. for 18 hours with shaking. Turbidity was measured and compared with a previously prepared calibration curve so that an appropriate aliquot could be used to make 10 ml of an inoculum containing $1 \times 10^5$ colony forming units/ml. Each test swatch was inoculated with 560 µl of this bacterial suspension in phosphate buffered saline. The inoculum was also serially diluted and plated.

The test swatches used were cut aseptically into 1.5 inch squares and placed into sterile 60 mm Petri dishes. As a control, the bacterial recovery was occasionally performed without any added inoculum, with the finding that it was very uncommon to detect any bacteria even when the recovery fluid was plated directly.

Four swatches of each material were inoculated, half being placed under the light source and the other plate being wrapped in aluminum foil to keep them dark. The light source was a 500 watt photoflood lamp with reflector (photoflood lamp ECT, 3200K with 10–12" reflector) set 15 inches above a bench top in a 4° C. cold room. A 9" square Pyrex baking dish filled with cold water was interposed between the lamp and the samples to absorb heat and any ultraviolet irradiation. Samples were illuminated for a defined period of time, generally one hour unless otherwise noted below. While the samples were being illuminated, the last two swatches were inoculated and immediately started through the recovery procedure in order to find the bacterial count at zero time.

For the recovery procedure, samples were aseptically transferred into a sterilized 125×20 mm capped tube containing about a dozen 3 mm glass beads and 5 ml of sterile phosphate buffered saline. The cap was sealed and the tube shaken vigorously for one minute and then placed in a low intensity ultrasonic cleaning bath (Branson model 3200) for 30 seconds. Serial tenfold dilutions were prepared from recovery fluid and each dilution was plated in duplicate with tempered tryptic soy agar in 60 mm plastic Petri plates. One ml of the recovery fluid was also plated directly (in duplicate) in a 100 mm Petri plate. Plates were incubated at 30° C. for one to two days until countable.

The zero time counts recovered from the swatches were compared with the inoculum count. All of the zero time contents were combined by averaging their base 10 logarithms to obtain and average log zero time reading. The four counts for each test condition (duplicate platings for each of the pair of samples) were also combined by averaging the base 10 logarithms of the bacterial counts. A logarithmic scale of killing efficiency, log reduction, was calculated as the difference between the sample and average zero time logarithms. Percent kill was calculated as $100*(1-10^{(log\ reduction)})$.

In the Tables that follow, the following abbreviations have the meaning indicated:

DI WAT—deionized water
Elvanol—8% solution of DuPont's Elvanol® 71–30 (a medium viscosity, fully hydrolyzed grade of polyvinyl alcohol
EPS—Union Carbide's UCARSIL® EPS silicone hydrophilic finish
BLUE GPN—BASF Corp., Calcotone Blue GPN Paste Pigment
Violet R—Ciba-Geigy Corp. Unisperse Violet R RW-767-P Pigment Yellow 26—Diarylide Yellow Pigment from Huls American Inc., Stabiloid 833-2826

IPA—isopropyl alcohol

WB4000—Hampshire Chemical Corp. DARATHANE® WB-4000 blocked waterborne polyurethane prepolymer

EXAMPLE 1

This example confirms the antimicrobial effects of Rose Bengal when bound to a substrate.

Fort Howard grade X-173 at 85 gsm (grams per square meter) air laid nonwoven that contains 100% cellulosic fiber with 20 to 30% acrylic latex binder was saturated at 150% wet pick-up with each of the formulas listed in Tables 1 and 2 below. After saturating, the wet hand sheets were dried for 90 seconds at 300° F. in an air circulating laboratory oven. After one hour exposure to light at 2000 foot candles intensity (equivalent to the light intensity for a hospital surgical field illumination), the Rose Bengal treated samples killed 99% of the microorganism *Staphylococcus aureus*. Swatches of the treated samples were washed in deionized water to check for leaching. Only the samples in which Darathane® WB4000 was used as the binding system showed no leaching. The results are shown in Table 3.

EXAMPLE 2

Bezman et al., "Photodynamic Inactivation of *E. coli* by Rose Bengal Immobilized on Polystyrene Beads", *Photochemistry and Photobiology*, 28, 325–329 (1978) purport to show that Rose Bengal immobilized on polystyrene beads is quite active at killing E. coli. As they note on page 327 of their publication, this result is at odds with earlier studies on photoinactivation.

This Example demonstrates that Rose Bengal beads are ineffective in producing antimicrobial results.

Rose Bengal which is covalently bound to a polystyrene support was obtained from Polysciences, Inc., 400 Valley Road, Warrington, Pa. 19876 (catalog #09789). The manufacturer confirmed that this material is at least 3% by weight Rose Bengal.

The activity of 60 mg of Polysciences, Inc, Rose Bengal beads was compared to drape samples containing either Rose Bengal or Toluidine Blue-O (Tables 46–48 and 50) using the standard procedure and spreading the beads into a monolayer in place of the test swatch. The beads gave only a slight reduction in counts (0.7 log units) whereas the drape samples reduced the bacterial counts greater than 3 log units, i.e., the drapes were more than 1000-fold more active than the beads. The amount of Rose Bengal present in the 60 mg of beads was at least 2 mg, whereas the drape samples contained only 2 μg. Thus, the immobilized Rose Bengal exhibited only 1/1,000,000 the activity of the Rose Bengal in the present invention.

EXAMPLE 3

This experiment demonstrates the effect of different dye-to-binder ratios on the microbial kill.

Hand sheets of Merfin 60850 nonwoven at 85 gsm were saturated at 150% wet pick-up with the formulas set forth in Tables 4–6. After saturating, the wet hand sheets were dried for 90 seconds at 300° F. in an air circulating laboratory oven. The final composition of the treated nonwovens is shown in Table 7. Samples were tested for physical properties and microbiological kill properties. The results are shown in Table 8. The % kill for the nonwoven in experiment 3057-44-1 is excellent, with over 99.99% of the *Staphylococcus aureus* bacteria killed upon exposure to 2000 fc illumination for one hour. This was accomplished with only 0.0012% Rose Bengal light activated antimicrobial on the nonwoven. When the level of light activated antimicrobial on the nonwoven remains constant but the antimicrobial dye to binder ratio is decreased, the % kill drops off in value. When higher amounts of binder are used to bind the dye to the nonwoven, lower kill values can be expected.

EXAMPLE 4

Walkisoft nonwoven material was saturated as a continuous web on a pilot line saturator with the formulas set forth in Tables 9–16 at 150% wet pick-up and oven dried at 275° F. to 300° F. at 7 feet per minute. The final composition of the treated nonwovens is shown in Table 17, and the antimicrobial effects are shown in Tables 18–20.

All of the samples killed greater than 99% of the *Staphylococcus aureus* bacteria in one hour after exposure to 2000 fc light. Some of the samples not exposed to light showed antimicrobial activity; these samples had no binder, which allowed the light activated dye to leach out into the microbial solution during the recovery procedure. Since the recovery procedure is conducted in the presence of light, the dye is photoactivated and kills some of the bacteria. The Rose Bengal treated samples did not show any significant activity against *Klebsiella pneumoniae* bacteria, however, the Toluidine Blue O samples were able to kill greater than 99% of the *Kp* bacteria in 24 hours. There was insufficient room light or leachate from the "no light" samples to kill any of the *Klebsiella pneumoniae* bacteria during the recovery procedure (Table 20).

Two of the samples (Table 18) were tested under room light against Methicillin resistant *Staphylococcus aureus* (MRSA). The Toluidine Blue O treated sample had a significant (80%) kill after 30 minutes under room lighting conditions and a very significant kill (99.8%) after 60 minutes. The Rose Bengal treated nonwoven did not have any significant kill (60%) even after one hour under room lights. When the samples were challenged with MRSA under bright light, all the samples had very significant kill rates after 60 minutes exposure (Table 19). There was evidence of Rose Bengal leaching when no binder was used, as seen by the antimicrobial activity in the "No Light" samples that get enough light in the recovery process to become active in killing MRSA. Also, the control sample which is not treated with any light activated dye shows antimicrobial activity if it is not washed before testing. This may be caused by the catalyst for the nonwoven binder, oxalic acid, which is also considered an antimicrobial.

EXAMPLE 5

To 598.7 grams of deionized water was added with mixing 9.4 grams of a 0.1% solution of Toluidine Blue O (TBO). To this mixture was added 91.9 grams of a 0.5% solution of Viscarin® SD398, a carrageenan from FMC. This order of addition must be followed or the TBO will precipitate out of solution if the carrageenan is added before the TBO. Hand sheets of Walkisoft WA-1 nonwoven at 85 gsm were saturated at 150% wet pick-up with the formula in Table 21. After saturating, the web hand sheets were dried for 90 seconds at 300° F. in an air circulating laboratory oven. The final composition of the dried nonwoven is shown in Table 22. The binding power of the Viscarin® for the dye was measured by placing a one gram sample of the treated nonwoven in a 4 ounce glass jar with 50 grams of deionized water. The jar with the lid on was shaken for 30 seconds by hand. There was a slight amount of foam on the top of the water but there was no visual indication of any blue color in the water that would indicate leaching.

Colorfastness to Crocking (AATCC Test Method 8-1989) was measured at 4.5 on the Gray Scale for Staining using 1 normal saline to wet the test cloth before running the test on the treated nonwoven. This means that very little color was transferred to the test cloth as a result of the crocking test. The absorbency of the treated nonwoven was measured by placing one drop of deionized water on the dry, treated nonwoven and measuring the amount of time it takes for the drop to completely soak into the nonwoven. The drop was absorbed instantly into the nonwoven. All of the testing on this treated nonwoven indicates that it is superior to the treated nonwovens where WB4000 was used as the binder for the dye. An important advantage of the use of Viscarin as the binder is that addition to the binder system of a wetting agent is not necessary for applications where good absorbency is required. Wetting agents can cause leaching of the dye and poorer crocking tests results.

EXAMPLE 6

To 597 grams of deionized water was added with mixing 11.4 grams of a 0.092% solution of Rose Bengal. To this mixture was added 91.6 grams of a 0.5% solution of Nalkat 7607, a polyquaternary amine chloride. This order of addition must be followed or the Rose Bengal will precipitate out of solution if the polyamine is added before the Rose Bengal. Hand sheets of Walkisoft WA-1 nonwoven at 85 gsm were saturated at 160% wet pick-up with the formulas in Tables 23–28. After saturating, the wet hand sheets were dried for 90 seconds at 300° F. in an air circulating laboratory oven. The final composition of the dried nonwovens are shown in Table 29. The binding power of the polyamine for the dye was measured by placing a one gram sample of the treated nonwoven in a 4 ounce glass jar with 50 grams of deionized water. The jar with the lid on was shaken for 30 seconds by hand. There was a slight amount of foam on the top of the water but there was no visual indication of any pink color in the water that would indicate leaching, except for sample 3046-96-4 which had a very slight pink color. When the level of the polyamine is too low, the saturating bath becomes unstable and the dye precipitates out of solution. Saturant 3046-96-5 was unstable because of the low polyamine level used in the formulation. The absorbency of the treated nonwoven was measured by placing one drop of deionized water on the dry, treated nonwoven and by measuring the amount of time it takes for the drop to completely soak into the nonwoven. Sample 3046-96-1 took 30 seconds for a drop of water to be absorbed, 3046-96-2 took 20 seconds, as did sample 3046-96-3, and sample 3046-96-4 took 6 seconds. Even 6 seconds is too long for most absorbent applications without the addition of a wetting agent in the treatment to improve absorbency. Most of the testing on this treated nonwoven indicates that it may be superior to the treated nonwovens where WB4000 was used as the binder for the dye. Thus, polyamine binder systems can be used for anionic light-activated antimicrobial dye systems. A wetting agent may be needed depending upon the water absorbency characteristics of the binder system.

EXAMPLE 7

Hand sheets of Fort Howard X-173 and Merfin grade 60850 nonwovens at 85 gsm were saturated at 140% wet pick-up with the formulas in Tables 31–34. After saturating, the wet hand sheets were dried for 90 seconds at 300° F. in an air circulating laboratory oven. The final composition of the treated nonwovens is shown in Table 35.

The TBO treated nonwoven was very effective against all bacteria tested: *Escherichia coli, Pseudomonas aeruginosa, Enterobacter cloacae, Staphylococcus aureus, Enterococcus faecalis, Klebsiella pneumoniae, Salmonella typhimurium, Staphylococcus epidermidis, Serratia marcescens*, and *Proteus vulgaris*, almost all cases killing greater than 99% of the bacteria in one hour. See Tables 36 through 45. There was good recovery of all the bacteria at time "0" which means that the treated nonwoven is not immediately toxic to bacteria. The treated nonwoven also did not show significant kill against the bacteria in the dark which also indicates that (1) light is needed to activate the antimicrobial properties of the TBO treatment, and (2) the treated nonwoven is not toxic to the bacteria.

The TBO treated samples (1815-95-2 & 4) were tested for leaching of the dye. One gram of treated nonwoven was placed in 200 ml of deionized water and allowed to soak overnight. There was no detectable leaching of the dye. The same test was repeated with phosphate buffered saline. Using a visible spectrophotometer, 1.3 ppm leaching from sample 1815-95-2 was measured, and 3.3 ppm leaching from sample 1815-95-4 was measured. This represents 6.8% and 17.4%, respectively, of the amount of dye present in one gram of treated nonwoven. These Teachings numbers indicate that the combination of binder and wetting agent are not good enough in holding the dye on the treated nonwoven.

EXAMPLE 8

A pilot saturator was set up with a deep pan saturator in line with a pilot equipment oven. The pan was filled with about 9100 grams of buffer solution having a pH of 7.126 before saturating the nonwoven. Walkisoft J80 nonwoven was saturated at 150% wet pick up (0.006 mils gap setting on the squeeze rolls) at 6 feet per minute and dried in the pilot oven at 275° F. to 300° F. The excess buffer solution is squeezed out by squeeze rolls and flows back into the saturator pan. After saturating 50 yards of material one foot wide, the saturating was stopped. The pH of the remaining buffer solution in the pan was almost the same as the starting pH (final pH of 6.975). The buffered and dried nonwoven was resaturated and rinsed with deionizecd water and dried in the oven while allowing deionized water to flow into the pan and out through a drain in the bottom of the pan. This process was repeated a second time in order to rinse out any excess buffer remaining in the nonwoven. Five gallons of deionized water was used for each rinse pass. The pan was then filled with 7000 grams of saturant (Tables 46 and 47). The buffered and rinsed nonwoven (sample 3046-76) was saturated at 150% wet pick up and dried in the pilot oven at 275° F. to 300° F. at 6 feet per minute. The final composition of the treated nonwovens is shown in Table 48.

The Rose Bengal and TBO treated nonwoven samples each killed 99.95% of the Methicillin Resistant *Staphylococcus aureus* after one hour exposure to intense light. Both control samples, washed and unwashed nonwoven, barely showed any kill in light or dark (see Table 50). Only the TBO treated sample killed any *Klebsiella pneumoniae* bacteria with an 84% kill.

Samples of the treated and untreated nonwovens having the composition shown in Table 48 were loaded with HIV-1 in accordance with the following procedure.

Virus

The HTLV-IIIB strain of HIV-1 is propagated in the human T-lymphocyte cell line, H9 (Popovic, M. et al., Science 224:497–500, 1984). The virus inoculum consisted of supernatant fluids from H9-IIIB producer cultures.

Cells and Media

The cells used for routine screening were the MT-2 (Harada et al., Science 229:563–566 (1985) and CEM (Nara and Fischinger, Nature 332:469–470 (1988) cell lines. Cells were grown in RPMI 1640 medium supplemented with 20% (v/v) fetal calf serum (H9 cells) or 10% fetal calf serum (MT-2 and CEM cells). The medium also contained 100 units/ml penicillin, 100 mcg/ml streptomycin, and 25 mM HEPES buffer. The medium used for dilution of drugs and maintenance of cultures during the assay was the same as the above 10% serum. Cultures were maintained in disposable tissue culture labware at 37° C. in a humidified atmosphere at 5% $CO_2$ in air.

Reagents for Colorimetric Assay

MTT is a tetrazolium dye that is taken up and metabolized by live cells. The cells were subsequently lysed and the dye was released into the medium. The samples were then read on a microplate reader.

Protocol for Antiviral Assay

I. Drug Dilution and Addition to Plates
   1. Drugs were dissolved in DMSO at 40 mg/ml or in sterile deionized water at 2 mg/ml, unless otherwise specified.
   2. Drug dilutions were made in medium. Drugs in DMSO were initially diluted 1/200; drugs in water were diluted 1/10. Subsequent dilutions were made in log of 0.5 log series. The first screen on a drug was usually performed in log dilutions.
   3. Each dilution was added to plates in the amount of 100 $\mu$l/well. Drugs were tested in triplicate wells per dilution with infected cells, and in duplicate wells per dilution with uninfected cells for evaluation of cytotoxicity.
   4. After addition of cells to plates, the high drug concentration was 100 $\mu$l/ml. The high DMSO concentration was 0.25%.

II. Infection and Distribution of Cells to Microtiter Plates
   1. A viable cell count (trypan blue) was performed on the cells to be used.
   2. The desired total number of polybrene treated cells was placed in a 50 ml conical centrifuge tube (sterile, disposable), and virus was added to give a MOI of 0.03 $TCID_{50}$/ cell on MT-2 cells and approximately 0.12 $TCID_{50}$/cell on CEM cells. Fresh medium was added to adjust the cell density to $1 \times 10^5$ cells/ml, and the virus-cell suspension was incubated at 37° C. for 1–2 hours until ready for plating.
   3. Uninfected cells were prepared in the same manner but without addition of virus.
   4. Cell pellets were collected by low speed centrifugation and supernates were discarded.
   5. Infected and uninfected cells were resuspended in appropriate volume of medium and added to plates in the amount of 100 $\mu$l/well to give a starting cell number of 1 a $10^4$ cells/well.
   6. Plates are incubated for 7 days in a humidified atmosphere at 5% $CO_2$ in air.

III. Quantitation of Viral Cytopathic Effect and Drug Activity

On day 7 post-infection the viable cells were measured with a tetrazolium salt, MTT (450 micrograms per ml) added to the test plates. A solution of 10% SDS in 0.01 normal HCl was used to dissolve the MTT formazan produced. The optical density value is a function of the amount of formazan produced which is proportional to the number of viable cells. Plates were read at a wave-length of 570 nm on a $V_{max}$ plate reader (Molecular Devices). The percent inhibition or viral cytopathic effect (CPE) per drug concentration was measured as test over control and expressed in percent.

The virus loaded samples were evaluated for viable organisms after 6, 20 and 60 minute exposure in the dark, and after exposure to light (2000 foot candles) (Table 49). After six minutes in the dark, none of the samples show any kill of the HIV-1, however, after six minutes in the light, the light activated dye treated samples (Rose Bengal and TBO) kill 99% or more virus (Table 49). The untreated control shows only a 50% kill of virus in the light after six minutes. This is clear evidence that the TBO and Rose Bengal treated nonwovens exhibit light activated virucidal efficacy. The fact that there is little difference between the samples in the dark and the samples in the light after 60 minutes indicates that the inherent virucidal activity of the untreated nonwoven is still present although the rate of viral kill is slower for the untreated nonwoven.

Because of the high kill of the control sample in Table 49, the study was repeated comparing HIV-1 virus suspended in phosphate buffered saline (PBS) to HIV-1 virus suspended in whole human blood (Table 51). Again the control sample showed high kill rates in the dark and in the light at 20 and 60 minutes contact with the sample when the HIV-1 virus was suspended in PBS. When the HIV-1 virus is suspended in whole human blood, the control sample (3046-76) shows little or no activity against the virus. The Rose Bengal treated sample (3046-77-2) also shows little or no more activity than the control sample when exposed to HIV-1 suspended in whole human blood. In contrast, the Toluidine Blue-O treated sample (3046-77-1) showed essentially no activity in the dark and high kill rates when exposed to light for 20 and 60 minutes. The difference between the Rose Bengal and Toluidine Blue-O against HIV-1 suspended in blood is attributed to the fact that blood absorbs light in the region of the visible spectrum where Rose Bengal absorbs light., and Toluidine Blue-O absorbs light beyond the range where blood absorbs light. Therefore, Toluidine Blue-O is active in the presence of blood.

EXAMPLE 9

Hand sheets of Walkisoft WA-2 nonwoven at 85 gsm were saturated at 150% wet pick-up with the formulas in Tables 52–62. After saturating, the wet hand sheets were dried for 90 seconds at 300° F. in an air circulating laboratory oven. Samples were evaluated for crocking and leaching and for virucidal kill properties. The final composition of the treated nonwovens is shown in Table 63.

The binding power of the Viscarin® for the dye was measured by placing a one gram sample of the treated nonwoven in a 4 ounce glass jar with 50 grams of deionized water. The jar with the lid on was shaken for 30 seconds by hand. There was no visual indication of any blue color in the water for the highest TBO or Methylene Blue dye with the highest level of binder, Viscarin®, evaluated, as shown in Table 64. Thus, the binder system is working well in holding the dyes onto the cellulose fiber in the nonwoven.

Colorfastness to Crocking (AATCC Test Method 8-1989) was measured on the Gray Scale for Staining using 1 normal saline to wet the test cloth before running the test on the treated nonwoven. The minimum value acceptable for this test is 2.3 and the target is 3.8 or higher. No color transfer to the test cloth is rated at 5.0, the highest possible rating for this test. Samples 3057-30-(1A, 1B, 1C, 3A, 3B, and 3C)

containing either TBO or MB were rated at 4.5 on the Gray Scale (See Table 64). This means that very little color transferred to the test cloth as a result of the crocking test. With the higher level of binder, Viscarin®, and the higher level of dye, the crocking results begin to drop off (4.0 for TBO and 3.5 for MB). This means that even though the crocking results are still within specification, the limit of the binding power for this type of nonwoven treatment system is being approached. The TH dye was evaluated at 3.5 for the lowest dye level and the lowest binder level. Also, the saturant bath system was unstable and had to be stirred constantly to prevent separation.

Table 65 shows the % kill results against HIV-1. All of the samples gave greater than 99% kill after 15 minutes of contact with HIV-1 suspended in whole human blood and exposure to 2000 foot candles illumination. The untreated control samples showed no virucidal activity. In addition, the nonwoven sample treated with a blend of all three dyes, TBO-TH-MB, also killed greater than 99% of the virus present.

EXAMPLE 10

Some of the nonwovens prepared in Example 9 were exposed to H9 cells chronically infected with HIV-1 and suspended in whole human blood. After two hours exposure to 2000 foot candles illumination, all but one of the dye treated nonwoven samples gave greater than 99% virus kill, as shown in Table 66. The highest kill, 99.94%t or greater, was for Methylene Blue at 80 ppm with Viscarin® as the binder. There was good recovery of virus for the zero time control. Based on all of the dye results, Methylene Blue gave the highest kill rates at comparable dye levels.

TABLE 1

Experiment No.: 1811-48-1

| INGREDIENT | WET AMOUNT | SOLIDS % | WET % | DRY WEIGHT | DRY % |
|---|---|---|---|---|---|
| DI WAT | 250.6000 | | 78.1635 | | |
| ELVANOL | 66.6000 | 8.0000 | 20.7729 | 5.3280 | 74.8189 |
| EPS | 1.6000 | 100.0000 | 0.4990 | 1.6000 | 22.4681 |
| IPA | 1.6000 | | 0.4990 | | |
| ROSE BENGAL | 0.2100 | 92.0000 | 0.0655 | 0.1932 | 2.7130 |
| TOTAL: | 320.6100 | 2.2211 ACTUAL % SOLIDS | 100.0000 | 7.1212 | 100.0000 |

TABLE 2

Experiment No.: 1811-48-4

| INGREDIENT | WET AMOUNT | SOLIDS % | WET % | DRY WEIGHT | DRY % |
|---|---|---|---|---|---|
| DI WAT | 256.0000 | | 79.9475 | | |
| WB4000 | 64.0000 | 40.0000 | 19.9869 | 25.6000 | 99.2510 |
| ROSE BENGAL | 0.2100 | 92.0000 | 0.0656 | 0.1932 | 0.7490 |
| TOTAL: | 320.2100 | 8.0551 ACTUAL % SOLIDS | 100.0000 | 25.7932 | 100.0000 |

TABLE 3

REFERENCE NO.: E 1811-48 WRC 16043-30

DYE: Rose Bengal
LIGHT EXPOSURE 120 min.
TIME:
MICROORGANISM: Staph.
Light Level: 2000 fc
Samples were washed in water to check for leaching.

| RUN # | DARK LOG # | | LIGHT LOG # | | LIGHT % KILL | COMMENTS SUBSTRATE | Wash water absorbance at 546 nanometers |
|---|---|---|---|---|---|---|---|
| 1 | 3.1 | < | 0.5 | > | 99.7488 | Nonwoven X-173 | 0.90 |
| 4 | 4.6 | ~ | 1 | ~ | 99.9749 | Nonwoven X-173 | 0.00 |

TABLE 4

EXPERIMENT No. 3057-44-1

SUBSTRATE: Merfin 60850
BASIS WEIGHT-GSM: 85

| INGREDIENT | WET AMOUNT | SOLIDS % | WET % | DRY WEIGHT | DRY % |
|---|---|---|---|---|---|
| DI WAT | 319.0000 | | 99.6742 | | |
| WB4000 | 1.0000 | 40.0000 | 0.3125 | 0.4000 | 90.3751 |
| ROSE BENGAL | 0.0026 | 100.0000 | 0.0008 | 0.0026 | 0.5874 |
| FD&C BLUE #2 | 0.0400 | 100.0000 | 0.0125 | 0.0400 | 9.0375 |
| TOTAL: | 320.0426 | 0.1383 ACTUAL % SOLIDS | 100.0000 | 0.4426 | 100.0000 |

TABLE 5

EXPERIMENT No. 3057-44-2

SUBSTRATE: Merfin 60850
BASIS WEIGHT-GSM: 85

| INGREDIENT | WET AMOUNT | SOLIDS % | WET % | DRY WEIGHT | DRY % |
|---|---|---|---|---|---|
| DI WAT | 318.0000 | | 99.3618 | | |
| WB4000 | 2.0000 | 40.0000 | 0.6249 | 0.8000 | 94.9442 |
| ROSE BENGAL | 0.0026 | 100.0000 | 0.0008 | 0.0026 | 0.3086 |
| FD&C BLUE #2 | 0.0400 | 100.0000 | 0.0125 | 0.0400 | 4.7472 |
| TOTAL: | 320.0426 | 0.2633 ACTUAL % SOLIDS | 100.0000 | 0.8426 | 100.0000 |

TABLE 6

EXPERIMENT No. 3057-44-3

SUBSTRATE: Merfin 60850  
BASIS WEIGHT-GSM: 85

| INGRE-DIENT | WET AMOUNT | SOLIDS % | WET % | DRY WEIGHT | DRY % |
|---|---|---|---|---|---|
| DI WAT | 316.0000 |  | 98.7369 |  |  |
| WB4000 | 4.0000 | 40.0000 | 1.2498 | 1.6000 | 97.4066 |
| ROSE BENGAL | 0.0026 | 100.0000 | 0.0008 | 0.0026 | 0.1583 |
| FD&C BLUE #2 | 0.0400 | 100.0000 | 0.0125 | 0.0400 | 2.4352 |
| TOTAL: | 320.0426 | 0.5132 ACTUAL % SOLIDS | 100.0000 | 1.6426 | 100.0000 |

TABLE 7

% COMPOSITION by WEIGHT

| Experiment No. | Nonwoven 60850 | Binder WB-4000 | Dyes/Antimicrobials RB | Other Components FD&C BLUE #2 | Dye/Binder Ratio |
|---|---|---|---|---|---|
| 3057-44-1 | 99.793 | 0.1871 | 0.0012 | 0.0187 | 0.00641 |
| 3057-44-2 | 99.6066 | 0.3735 | 0.0012 | 0.0187 | 0.00321 |
| 3057-44-3 | 99.236 | 0.7442 | 0.0012 | 0.0186 | 0.00161 |

TABLE 8

REFERENCE NO.: E 3057-44-(1–3) WRC 16043-91

DYE: Rose Bengal  
LIGHT EXPOSURE TIME: 60 min.  
MICROORGANISM: Staph.  
Light Level: 2000 fc  
Nonwoven-Merfin 60850

| RUN # | Time '0' LOG # | DARK LOG # | LIGHT LOG # | LIGHT % KILL | COMMENTS |
|---|---|---|---|---|---|
| 1 | 5.1 | 4.9 | < 1.0 | > 99.991 | No Leaching of Rose Bengal, FD&C Blue #2 leached |
| 2 | 5.0 | 4.7 | < 2.3 | > 99.815 | No Leaching of Rose Bengal, FD&C Blue #2 leached |
| 3 | 5.0 | 4.7 | < 3.5 | > 97.071 | No Leaching of Rose Bengal, FD&C Blue #2 leached |
| Ave. | 5.0 |  |  |  | Log Seed Bacteria = 5.0 |

TABLE 9

EXPERIMENT No. 3046-34-1

SUBSTRATE: J81  
BASIS WEIGHT-GSM: 85

| INGRE-DIENT | WET AMOUNT | SOLIDS % | WET % | DRY WEIGHT | DRY % |
|---|---|---|---|---|---|
| DI WAT | 6,921.1000 |  | 98.8729 |  |  |
| WB4000 | 22.2000 | 39.5000 | 0.3171 | 8.7690 | 99.3576 |
| ROSE BENGAL | 56.7000 | 0.1000 | 0.8100 | 0.0567 | 0.6424 |
| TOTAL: | 7,000.0000 | 0.1261 ACTUAL % SOLIDS | 100.0000 | 8.8257 | 100.0000 |

TABLE 10

EXPERIMENT No. 3046-34-2

SUBSTRATE: J81  
BASIS WEIGHT-GSM: 85

| INGRE-DIENT | WET AMOUNT | SOLIDS % | WET % | DRY WEIGHT | DRY % |
|---|---|---|---|---|---|
| DI WAT | 6,943.3000 |  | 99.1900 |  |  |
| ROSE BENGAL | 56.7000 | 0.1000 | 0.8100 | 0.0567 | 100.0000 |
| TOTAL: | 7,000.0000 | 0.0008 ACTUAL % SOLIDS | 100.0000 | 0.0567 | 100.0000 |

TABLE 11

EXPERIMENT No. 3046-34-3

SUBSTRATE: J81  
BASIS WEIGHT-GSM: 85

| INGRE-DIENT | WET AMOUNT | SOLIDS % | WET % | DRY WEIGHT | DRY % |
|---|---|---|---|---|---|
| DI WAT | 6,894.6000 |  | 98.4943 |  |  |
| WB4000 | 11.6000 | 39.5000 | 0.1657 | 4.5820 | 97.9939 |
| TBO | 93.8000 | 0.1000 | 1.3400 | 0.0938 | 2.0061 |
| TOTAL: | 7,000.0000 | 0.0668 ACTUAL % SOLIDS | 100.0000 | 4.6758 | 100.0000 |

TABLE 12

EXPERIMENT No. 3046-34-4

SUBSTRATE: J81  
BASIS WEIGHT-GSM: 85

| INGRE-DIENT | WET AMOUNT | SOLIDS % | WET % | DRY WEIGHT | DRY % |
|---|---|---|---|---|---|
| DI WAT | 6,906.2000 |  | 98.6600 |  |  |
| TBO | 93.8000 | 0.1000 | 1.3400 | 0.0938 | 100.0000 |
| TOTAL: | 7,000.0000 | 0.0013 ACTUAL % SOLIDS | 100.0000 | 0.0938 | 100.0000 |

TABLE 13

EXPERIMENT No. 3046-34-5

SUBSTRATE: J81  
BASIS WEIGHT-GSM: 85

| INGREDIENT | WET AMOUNT | SOLIDS % | WET % | DRY WEIGHT | DRY % |
|---|---|---|---|---|---|
| DI WAT | 6,842.0000 | | 97.7429 | | |
| WB4000 | 44.3000 | 39.5000 | 0.6329 | 17.4985 | 99.3544 |
| ROSE BENGAL | 113.7000 | 0.1000 | 1.6243 | 0.1137 | 0.6456 |
| TOTAL: | 7,000.0000 | 0.2516 ACTUAL % SOLIDS | 100.0000 | 17.6122 | 100.0000 |

TABLE 14

EXPERIMENT No. 3046-34-6

SUBSTRATE: J81  
BASIS WEIGHT-GSM: 85

| INGREDIENT | WET AMOUNT | SOLIDS % | WET % | DRY WEIGHT | DRY % |
|---|---|---|---|---|---|
| DI WAT | 6,886.3000 | | 98.3757 | | |
| ROSE BENGAL | 113.7000 | 0.1000 | 1.6243 | 0.1137 | 100.0000 |
| TOTAL: | 7,000.0000 | 0.0016 ACTUAL % SOLIDS | 100.0000 | 0.1137 | 100.0000 |

TABLE 15

EXPERIMENT No. 3046-34-7

SUBSTRATE: J81  
BASIS WEIGHT-GSM: 85

| INGREDIENT | WET AMOUNT | SOLIDS % | WET % | DRY WEIGHT | DRY % |
|---|---|---|---|---|---|
| DI WAT | 6,789.1000 | | 96.9871 | | |
| WB4000 | 23.3000 | 39.5000 | 0.3329 | 9.2035 | 98.0024 |
| TBO | 187.6000 | 0.1000 | 2.6800 | 0.1876 | 1.9976 |
| TOTAL: | 7,000.0000 | 0.1342 ACTUAL % SOLIDS | 100.0000 | 9.3911 | 100.0000 |

TABLE 16

EXPERIMENT No. 3046-34-8

SUBSTRATE: J81  
BASIS WEIGHT-GSM: 85

| INGREDIENT | WET AMOUNT | SOLIDS % | WET % | DRY WEIGHT | DRY % |
|---|---|---|---|---|---|
| DI WAT | 6,812.4000 | | 97.3200 | | |
| TBO | 187.6000 | 0.1000 | 2.6800 | 0.1876 | 100.0000 |
| TOTAL: | 7,000.0000 | 0.0027 ACTUAL % SOLIDS | 100.0000 | 0.1876 | 100.0000 |

TABLE 17

| | % COMPOSITION by WEIGHT | | | | |
|---|---|---|---|---|---|
| | Nonwoven | Binder | Dyes/Antimicrobials | | Dye/Binder |
| Experiment No. | J81 | WB4000 | RB | TBO | Ratio |
| 3046-34-1 | 99.8112 | .1876 | .0012 | | 0.0064 |
| 3046-34-2 | 99.9988 | | .0012 | | |
| 3046-34-3 | 99.8999 | .0981 | | .0020 | 0.0204 |
| 3046-34-4 | 99.9980 | | | .0020 | |
| 3046-34-5 | 99.6240 | .3736 | .0024 | | 0.0064 |
| 3046-34-6 | 99.9976 | | .0024 | | |
| 3046-34-7 | 99.7992 | .1968 | | .0040 | 0.0203 |
| 3046-34-8 | 99.9960 | | | .0040 | |

TABLE 18

REFERENCE NO.: 3046-34-5,7 WRC 17450-(28-30)  
DYE: RB & TBO  
LIGHT EXPOSURE TIME: 30 & 60 min. Light Level: Room Light  
MICROORGANISM: MRSA Substrate --Walkisoft J41

| RUN# | Time '0' LOG# | 30 min. DARK LOG # | 60 min. DARK LOG # | 30 min. LIGHT LOG # | 30 min. LIGHT % KILL | 60 min. LIGHT LOG # | 60 min. LIGHT % KILL | COMMENTS |
|---|---|---|---|---|---|---|---|---|
| | | | | | | | | Room Light Methicillin Resistant *Staphylococcus aureus*- Seed = 4.2 |
| 5 | 4.2 | 4.1 | 4.2 | 4.0 | 36.9043 | 3.8 | 60.1893 | WB4000 with Rose Bengal at 24 ppm |

TABLE 18-continued

REFERENCE NO.: 3046-34-5,7 WRC 17450-(28-30)
DYE: RB & TBO
LIGHT EXPOSURE TIME: 30 & 60 min.    Light Level: Room Light
MICROORGANISM MRSA    Substrate --Walkisoft J41

| RUN# | Time '0' LOG# | 30 min. DARK LOG # | 60 min. DARK LOG # | 30 min. LIGHT LOG # | 30 min. LIGHT % KILL | 60 min. LIGHT LOG # | 60 min. LIGHT % KILL | COMMENTS |
|---|---|---|---|---|---|---|---|---|
| 7 | 4.2 | 4.1 | 4.1 | 3.5 | 80.0474 | 1.5 | 99.8005 | WB4000 with Toluidine Blue O at 40 ppm |
| Control | 4.2 | 4.1 | 4.1 | 4.1 | 20.5672 | 4.2 | No Kill | Washed CA5 |

TABLE 19

REFERENCE NO.: 3046-34-(5-8) WRC 17450-(24-25)
DYE: RB & TBO
LIGHT EXPOSURE TIME: 60 min.    Light Level: 2000 fc
MICROORGANISM: MRSA    Substrate -Walkisoft J41

| RUN# | Time '0' LOG # | 60 min. DARK LOG # | 60 min. DARK % KILL | 60 min. LIGHT LOG # | 60 min. LIGHT % KILL | COMMENTS |
|---|---|---|---|---|---|---|
|  |  |  |  |  |  | Bright Light Methicillin Resistant *Staphylococcus aureus* - Seed = 4.5 |
| 5 | 4.4 | 4.3 | No Kill | 2.3 | ~99.00 | WB4000 with Rose Bengal at 24 ppm |
| 6 | 4.2 | < 1.0 | 99.9499 | 2.5 | 98.42 | No Binder; Rose Bengal at 24 ppm; |
| 7 | 4.3 | 4.2 | 20.5672 | 1.0 | > 99.95 | WB4000 with Toluidine Blue O at 40 ppm |
| 8 | 4.3 | 4.2 | 20.5672 | 1.0 | > 99.95 | No Binder; Toluidine Blue O at 40 ppm; Leached; gave kill in solution. |
| Control | 4.4 | 3.0 | 96.0189 | 3.4 | 90.00 | Unwashed CA5 |
| Average | 4.3 |  |  |  |  |  |

TABLE 20

REFERENCE No.: E 3046-34-(1–8) WRC 17253-59

DYE: RB & TBO
LIGHT EXPOSURE TIME: 60 min.
MICROORGANISM: Staph., Kp
Light Level: 2000 fc
Substrate--Walkisoft J41

| RUN # | Time '0' LOG # | 60 min. DARK LOG # | 60 min. DARK % KILL | 60 min. LIGHT LOG # | 60 min. LIGHT % KILL | COMMENTS |
|---|---|---|---|---|---|---|
|  |  |  |  |  |  | *Staphylococcus aureus*--Seed = 5. |
| 1 | 5.4 | 5.4 | No Kill | < 1.0 | > 99.9950 | WB4000 with Rose Bengal at 12 ppm |
| 2 | 4.9 | < 1.0 | > 99.9950 | < 1.0 | > 99.9950 | No Binder; Rose Bengal at 12 ppm; Leached; gave kill in solution. |
| 3 | 5.5 | 5.4 | 26 | < 1.0 | > 99.9950 | WB4000 with Toluidine Blue 0 at 20 ppm; Slight Leaching |
| 4 | 5.3 | 5.0 | 49.8813 | < 1.0 | > 99.9950 | No Binder; Toluidine Blue 0 at 20 ppm; Leached; gave kill in solution. |
| 5 | 5.4 | 5.4 | No Kill | 2.4 | 99.8741 | WB4000 with Rose Bengal at 24 ppm |
| 6 | 2.3 | < 1.0 | > 99.9950 | < 1.0 | > 99.9950 | No Binder; Rose Bengal at 24 ppm; Leached; gave kill in solution. |
| 7 | 5.5 | 5.5 | No Kill | < 1.0 | > 99.9950 | WB4000 with Toluidine Blue 0 at 40 ppm |
| 8 | 5.4 | 5.0 | 49.8813 | < 1.0 | > 99.9950 | No Binder; Toluidine Blue 0 at 40 ppm; Leached; gave kill in solution |
| Time '0' Avg. | 5.3 |  |  |  |  | #6 result omitted from Time '0' Average |
|  |  |  |  |  |  | *Klebsiella pneumoniae*--Seed = 5.2 |
| 1 | 5.1 | 5.2 | No Kill | 5.1 | No Kill | WB4000 with Rose Bengal at 12 ppm |
| 2 | 5.1 | 5.1 | No Kill | 5.1 | No Kill | No Binder; Rose Bengal at 12 ppm |
| 3 | 5.1 | 5.2 | No Kill | 4.2 | 87.4107 | WB4000 with Toluidine Blue 0 at 20 ppm |

TABLE 20-continued

REFERENCE No.: E 3046-34-(1–8) WRC 17253-59

DYE: RB & TBO
LIGHT EXPOSURE TIME: 60 min.
MICROORGANISM: Staph., Kp
Light Level: 2000 fc
Substrate--Walkisoft J41

| RUN # | Time '0' LOG # | 60 min. DARK LOG # | 60 min. DARK % KILL | 60 min. LIGHT LOG # | 60 min. LIGHT % KILL | COMMENTS |
|---|---|---|---|---|---|---|
| 4 | 5.1 | 5.2 | No Kill | 4.0 | 92.0567 | No Binder; Toluidine Blue 0 at 20 ppm |
| 5 | 5.1 | 5.2 | No Kill | 5.1 | No Kill | WB4000 with Rose Bengal at 24 ppm |
| 6 | 5.1 | 5.2 | No Kill | 4.7 | 60.1893 | No Binder; Rose Bengal at 24 ppm |
| 7 | 5.1 | 5.1 | No Kill | 2.5 | 99.7488 | WB4000 with Toluidine Blue 0 at 40 ppm |
| 8 | 5.1 | 5.1 | No Kill ~ | 2.4 ~ | 99.8005 | No Binder; Toluidine Blue 0 at 40 ppm |
| Time '0' Avg. | 5.1 | | | | | |

TABLE 21

EXPERIMENT No. 3046-92

SUBSTRATE: WA-1
BASIS WEIGHT-GSM: 85

| INGREDIENT | WET AMOUNT | SOLIDS % | WET % | DRY WEIGHT | DRY % |
|---|---|---|---|---|---|
| DI WAT | 598.7000 | | 85.5286 | | |
| TBO | 9.4000 | 0.1000 | 1.3429 | 0.0094 | 2.0047 |
| VISCARIN ® SD 389 | 91.9000 | 0.5000 | 13.1286 | 0.4595 | 97.9953 |
| TOTAL: | 700.0000 | 0.0670 ACTUAL % SOLIDS | 100.0000 | 0.4689 | 100.0000 |

TABLE 22

% COMPOSITION by WEIGHT

| Experiment No. | Nonwoven WA-1 | Dye Binder VIS389 | Dyes/Antimicrobials TBO | Dyes/Antimicrobials RB | Dye/Binder Ratio |
|---|---|---|---|---|---|
| 3046-92 | 99.8996 | 0.0984 | 0.0020 | | 0.0203 |
| 3046-93-1 | 99.8998 | 0.0980 | | 0.0022 | 0.0224 |

TABLE 23

EXPERIMENT No. 3046-96-1

SUBSTRATE: WA-1
BASIS WEIGHT-GSM: 85

| INGREDIENT | WET AMOUNT | SOLIDS % | WET % | DRY WEIGHT | DRY % |
|---|---|---|---|---|---|
| DI WAT | 597.0000 | | 85.2857 | | |
| ROSE BENGAL | 11.4000 | 0.0920 | 1.6286 | 0.0105 | 2.2387 |
| NALCO 7607 | 91.6000 | 0.5000 | 13.0857 | 0.4580 | 97.7613 |
| TOTAL: | 700.0000 | 0.0669 ACTUAL % SOLIDS | 100.0000 | 0.4685 | 100.0000 |

TABLE 24

EXPERIMENT No. 3046-96-2

SUBSTRATE: WA-1
BASIS WEIGHT-GSM: 85

| INGREDIENT | WET AMOUNT | SOLIDS % | WET % | DRY WEIGHT | DRY % |
|---|---|---|---|---|---|
| DI WAT | 642.8000 | | 91.8286 | | |
| ROSE BENGAL | 11.4000 | 0.0920 | 1.6286 | 0.0105 | 4.3793 |

TABLE 24-continued

EXPERIMENT No. 3046-96-2

SUBSTRATE: WA-1
BASIS WEIGHT-GSM: 85

| INGRE-DIENT | WET AMOUNT | SOLIDS % | WET % | DRY WEIGHT | DRY % |
|---|---|---|---|---|---|
| NALCO 7607 | 45.8000 | 0.5000 | 6.5429 | 0.2290 | 95.6207 |
| TOTAL: | 700.0000 | 0.0342 ACTUAL % SOLIDS | 100.0000 | 0.2395 | 100.0000 |

TABLE 25

EXPERIMENT No. 3046-96-3

SUBSTRATE: WA-1
BASIS WEIGHT-GSM: 85

| INGRE-DIENT | WET AMOUNT | SOLIDS % | WET % | DRY WEIGHT | DRY % |
|---|---|---|---|---|---|
| DI WAT | 682.8000 | | 97.5568 | | |
| ROSE BENGAL | 11.4000 | 0.0920 | 1.6288 | 0.0105 | 26.9006 |
| NALCO 7607 | 5.7000 | 0.5000 | 0.8144 | 0.0285 | 73.0994 |
| TOTAL: | 699.9000 | 0.0056 ACTUAL % SOLIDS | 100.0000 | 0.0390 | 100.0000 |

TABLE 26

EXPERIMENT No. 3046-96-4A

SUBSTRATE: 3096-94 (Buffered WA-1)
BASIS WEIGHT-GSM: 85

| INGRE-DIENT | WET AMOUNT | SOLIDS % | WET % | DRY WEIGHT | DRY % |
|---|---|---|---|---|---|
| DI WAT | 685.7000 | | 97.9571 | | |
| ROSE BENGAL | 11.4000 | 0.0920 | 1.6286 | 0.0105 | 41.9721 |
| NALCO 7607 | 2.9000 | 0.5000 | 0.4143 | 0.0145 | 58.0279 |
| TOTAL: | 700.0000 | 0.0036 ACTUAL % SOLIDS | 100.0000 | 0.0250 | 100.0000 |

TABLE 27

EXPERIMENT No. 3046-96-4B

SUBSTRATE: WA-1
BASIS WEIGHT-GSM: 85

| INGRE-DIENT | WET AMOUNT | SOLIDS % | WET % | DRY WEIGHT | DRY % |
|---|---|---|---|---|---|
| DI WAT | 685.7000 | | 97.9571 | | |
| ROSE BENGAL | 11.4000 | 0.0920 | 1.6286 | 0.0105 | 41.9721 |
| NALCO 7607 | 2.9000 | 0.5000 | 0.4143 | 0.0145 | 58.0279 |
| TOTAL: | 700.0000 | 0.0036 ACTUAL % SOLIDS | 100.0000 | 0.0250 | 100.0000 |

TABLE 28

EXPERIMENT No. 3046-96-5

SUBSTRATE: WA-1
BASIS WEIGHT-GSM: 85

| INGRE-DIENT | WET AMOUNT | SOLIDS % | WET % | DRY WEIGHT | DRY % |
|---|---|---|---|---|---|
| DI WAT | 687.2000 | | 98.1714 | | |
| ROSE BENGAL | 11.4000 | 0.0920 | 1.6286 | 0.0105 | 59.9726 |
| NALCO 7607 | 1.4000 | 0.5000 | 0.2000 | 0.0070 | 40.0274 |
| TOTAL: | 700.0000 | 0.0025 ACTUAL % SOLIDS | 100.0000 | 0.0175 | 100.0000 |

TABLE 29

| | % COMPOSITION by WEIGHT | | | | |
|---|---|---|---|---|---|
| Experiment | Nonwoven | | Dye Binder | Dye | Dye/Binder |
| No. | WA-1 | WA-1B | NAL7607 | RB | Ratio |
| 3046-96-1 | 99.8930 | | 0.1046 | 0.0024 | 0.0229 |
| 3046-96-2 | 99.9453 | | 0.0523 | 0.0024 | 0.0459 |
| 3046-96-3 | 99.9911 | | 0.0065 | 0.0024 | 0.3692 |
| 3046-96-4A | | 99.9943 | 0.0033 | 0.0024 | 0.7273 |
| 3046-96-4B | 99.9943 | | 0.0033 | 0.0024 | 0.7273 |
| 3046-96-5 | 99.9960 | | 0.0016 | 0.0024 | 1.5000 |

TABLE 30

REFERENCE NO.: E 3046-94, 95, 96 WRC 17450-(80-84)

DYE: RB & TBO  
LIGHT EXPOSURE 60 min.  
TIME:  
MICROORGANISM: MRSA  
Light Level: 2000 fc  
Substrate--Walkisoft WA-1 Raw & Buffered-Washed

| RUN # | Time '0' LOG # | DARK LOG # | | LIGHT LOG # | | LIGHT % KILL | COMMENTS | Dark % Kil |
|---|---|---|---|---|---|---|---|---|
| | | | | | | | Methicillin Resistant *Staphylococcus aureus*--Seed = 5.5 | |
| 94 | 5.5 | 5.3 | | 5.3 | | 34.4358 | Walkisoft WA-1 Buffered and Washed; Control | 34.435 |
| 95-1A | 5.5 | 5.3 | ~ | 1.3 | ~ | 99.9934 | Washed WA-1 Treated with WB4000 & TBO; 21 ppm | 34.435 |
| 95-1B | 5.5 | 5.4 | < | 1.0 | > | 99.9967 | Raw WA-1 Treated with WB4000 & TBO; 21 ppm | 17.459 |
| 95-2A | 5.5 | 5.1 | | 1.2 | | 99.9948 | Washed WA-1 Treated with WB4000 & RB; 24 ppm | 58.631 |
| 95-2B | 5.4 | 5.1 | < | 1.0 | > | 99.9967 | Raw WA-1 Treated with WB4000 & RB; 24 ppm | 58.631 |
| 95-4 | 5.5 | 5.0 | | 4.7 | | 83.5310 | Raw WA-1; Control | 67.140 |
| Average | 5.5 | | | | | | | |
| | | | | | | | Methicillin Resistant *Staphylococcus aureus*--Seed = 5.5 | |
| 95-1A | 5.5 | 5.3 | ~ | 1.4 | ~ | 99.9900 | Washed WA-1 Treated with WB4000 & TBO; 21 ppm | 20.567 |
| 95-2A | 5.4 | 5.3 | ~ | 1.5 | ~ | 99.9874 | Washed WA-1 Treated with WB4000 & RB; 24 ppm | 20.567 |
| 95-3A | 5.4 | 5.3 | ~ | 1.5 | ~ | 99.9874 | Washed WA-1 Treated with Viscarin ® & TBO; 21 ppm | 20.567 |
| 95-3B | 5.4 | 5.1 | ~ | 1.2 | ~ | 99.9937 | Raw WA-1 Treated with Viscarin ® & TBO; 21 ppm | 49.881 |
| 96-4A | 5.4 | 4.8 | < | 1.0 | > | 99.9960 | Washed WA-1 Treated with Nalco 7607 & RB; 24 ppm | 74.881 |
| 96-4B | 5.3 | 4.1 | < | 1.0 | > | 99.9960 | Raw WA-1 Treated with Nalco 7607 & RB; 24 ppm | 94.988 |
| Average | 5.4 | | | | | | | |

TABLE 31

EXPERIMENT No. 1815-95-1

SUBSTRATE: CA5  
BASIS WEIGHT-GSM: 85

| INGRE-DIENT | WET AMOUNT | SOLIDS % | WET % | DRY WEIGHT | DRY % |
|---|---|---|---|---|---|
| DI WAT | 4,791.7800 | | 99.8288 | | |
| WB4000 | 5.8800 | 40.0000 | 0.1225 | 2.3520 | 74.1722 |
| LEXAINE C | 2.3400 | 35.0000 | 0.0488 | 0.8190 | 25.8278 |
| TOTAL: | 4,800.0000 | 0.0661 ACTUAL % SOLIDS | 100.0000 | 3.1710 | 100.0000 |

TABLE 32

EXPERIMENT No. 1815-95-2

SUBSTRATE: CA5  
BASIS WEIGHT-GSM: 85

| INGRE-DIENT | WET AMOUNT | SOLIDS % | WET % | DRY WEIGHT | DRY % |
|---|---|---|---|---|---|
| DI WAT | 4,727.4600 | | 98.4888 | | |
| WB4000 | 5.8800 | 40.0000 | 0.1225 | 2.3520 | 72.6976 |
| LEXAINE C | 2.3400 | 35.0000 | 0.0488 | 0.8190 | 25.3143 |
| TBO | 64.3200 | 0.1000 | 1.3400 | 0.0643 | 1.9881 |
| TOTAL: | 4,800.0000 | 0.0674 ACTUAL % SOLIDS | 100.0000 | 3.2353 | 100.0000 |

TABLE 33

EXPERIMENT No. 1815-95-3

SUBSTRATE: MERFIN 60805  
BASIS WEIGHT-GSM: 85

| INGRE-DIENT | WET AMOUNT | SOLIDS % | WET % | DRY WEIGHT | DRY % |
|---|---|---|---|---|---|
| DI WAT | 4,791.7800 | | 99.8288 | | |
| WB4000 | 5.8800 | 40.0000 | 0.1225 | 2.3520 | 74.1722 |
| LEXAINE C | 2.3400 | 35.0000 | 0.0488 | 0.8190 | 25.8278 |
| TOTAL: | 4,800.0000 | 0.0661 ACTUAL % SOLIDS | 100.0000 | 3.1710 | 100.0000 |

TABLE 34

EXPERIMENT No. 1815-95-4

SUBSTRATE: MERFIN 60805  
BASIS WEIGHT-GSM: 85

| INGRE-DIENT | WET AMOUNT | SOLIDS % | WET % | DRY WEIGHT | DRY % |
|---|---|---|---|---|---|
| DI WAT | 4,727.4600 | | 98.4888 | | |
| WB4000 | 5.8800 | 40.0000 | 0.1225 | 2.3520 | 72.6976 |
| LEXAINE C | 2.3400 | 35.0000 | 0.0488 | 0.8190 | 25.3143 |
| TBO | 64.3200 | 0.1000 | 1.3400 | 0.0643 | 1.9881 |
| TOTAL: | 4,800.0000 | 0.0674 ACTUAL % SOLIDS | 100.0000 | 3.2353 | 100.0000 |

TABLE 35

% COMPOSITION by WEIGHT

| Experiment No. | Nonwoven X173 | Nonwoven 60850 | Binder WB4000 | Anti-microbials TBO | Wetting Agent LC | Dye/Binde Ratio |
|---|---|---|---|---|---|---|
| 1815-95-1 | 99.9076 | | .0685 | | .0239 | |
| 1815-95-2 | 99.9057 | | .0685 | .0019 | .0239 | 0.0277 |
| 1815-95-3 | | 99.9076 | .0685 | | .0239 | |
| 1815-95-4 | | 99.9057 | .0685 | .0019 | .0239 | 0.0277 |

TABLE 36

REFERENCE NO.: E 1815-95-(1–4) WRC 16502-(22 to 36)

DYE: TBO
LIGHT EXPOSURE TIME: 60 min.
MICROORGANISM: *E. coli*
Light Level: 2000 fc
Nonwoven-1815-95-(1&2) uses Fort Howard X-173
Nonwoven-1815-95-(3&4) uses Merfin 60850

| RUN # | Time '0' LOG # | DARK LOG # | LIGHT LOG # | LIGHT % KILL | COMMENTS |
|---|---|---|---|---|---|
| | | | | | *Escherichia coli*--Seed = 5.5 |
| 1 | 5.4 | 5.3 | 4.4 | 90.0000 | No TBO |
| 2 | 5.3 | 5.3 | < 1.0 > | 99.9950 | Toluidine Blue O = 19 ppm Total |
| 3 | 5.4 | 5.3 | 5.1 | 49.8813 | No TBO |
| 4 | 5.4 | 5.3 | < 1.0 > | 99.9960 | Toluidine Blue O = 19 ppm Total |

TABLE 37

REFERENCE NO.: E 1815-95-(1–4) WRC 16502-(22 to 36)

DYE: TBO
LIGHT EXPOSURE TIME: 60 min.
MICROORGANISM: Pa
Light Level: 2000 fc
Nonwoven-1815-95-(1&2) uses Fort Howard X-173
Nonwoven-1815-95-(3&4) uses Merfin 60850

| RUN # | Time '0' LOG # | DARK LOG # | LIGHT LOG # | % KILL | COMMENTS |
|---|---|---|---|---|---|
| | | | | | *Pseudomonas aeruginosa*--Seed = 5.1 |
| 1 | 5.0 | 4.9 | 4.9 | 20.5672 | No TBO |
| 2 | 5.0 | 4.9 | 2.7 | 99.4988 | Toluidine Blue O = 19 ppm Total |
| 3 | 4.9 | 4.7 | 4.9 | No Kill | No TBO |
| 4 | 4.9 | 4.9 | 4.0 | 87.4107 | Toluidine Blue O = 19 ppm Total |

TABLE 38

REFERENCE NO.: E 1815-95-(1–4) WRC 16502-(22 to 36)

DYE: TBO
LIGHT EXPOSURE TIME: 60 min.
MICROORGANISM: EC
Light Level: 2000 fc
Nonwoven-1815-95-(1&2) uses Fort Howard X-173
Nonwoven-1815-95-(3&4) uses Merfin 60850

| RUN # | Time '0' LOG # | DARK LOG # | LIGHT LOG # | LIGHT % KILL | COMMENTS |
|---|---|---|---|---|---|
| | | | | | *Enterobacter cloacae*--Seed = 6.2 |
| 1 | 6.1 | 6.1 | 5.9 | 36.9043 | No TBO |
| 2 | 6.0 | 5.7 | 3.0 | 99.9000 | Toluidine Blue O = 19 ppm Total |
| 3 | 6.1 | 6.1 | 5.9 | 36.9043 | No TBO |
| 4 | 6.0 | 5.9 | 2.0 | 99.9900 | Toluidine Blue O = 19 ppm Total |

TABLE 39

REFERENCE NO.: E 1815-95-(1–4) WRC 16502-(22 to 36)

DYE: TBO
LIGHT EXPOSURE TIME: 60 min.
MICROORGANISM: Sa
Light Level: 2000 fc
Nonwoven-1815-95-(1&2) uses Fort Howard X-173
Nonwoven-1815-95-(3&4) uses Merfin 60850

| RUN # | Time '0' LOG # | DARK LOG # | LIGHT LOG # | LIGHT % KILL | COMMENTS |
|---|---|---|---|---|---|
| | | | | | *Staphylococcus aureus*--Seed = 5.4 |
| 1 | 5.6 | 5.5 | 4.3 | 94.9881 | No TBO |
| 2 | 5.8 | 5.5 | < 1.0 > | 99.9984 | Toluidine Blue O = 19 ppm Total |
| 3 | 5.6 | 5.5 | 5.3 | 49.8813 | No TBO |
| 4 | 5.5 | 5.5 | < 1.0 > | 99.9968 | Toluidine Blue O = 19 ppm Total |

TABLE 40

REFERENCE NO.: E 1815-95-(1–4) WRC 16502-(22 to 36)

DYE: TBO
LIGHT EXPOSURE TIME: 60 min.
MICROORGANISM: Ef
Light Level: 2000 fc
Nonwoven-1815-95-(1&2) uses Fort Howard X-173
Nonwoven-1815-95-(3&4) uses Merfin 60850

| RUN # | Time '0' LOG # | DARK LOG # | LIGHT LOG # | LIGHT % KILL | COMMENTS |
|---|---|---|---|---|---|
| | | | | | *Enterococcus faecalis*--Seed = 5.7 |
| 1 | 5.6 | 5.1 | 5.0 | 74.8811 | No TBO |
| 2 | 5.6 | 5.1 | < 1.0 > | 99.9975 | Toluidine Blue O = 19 ppm Total |
| 3 | 5.4 | 5.2 | 5.3 | 20.5672 | No TBO |
| 4 | 5.3 | 5.2 | < 1.0 > | 99.9950 | Toluidine Blue O = 19 ppm Total |

TABLE 41

REFERENCE NO.: E 1815-95-(1–4) WRC 16502-(22 to 36)

DYE: TBO  
LIGHT EXPOSURE TIME: 60 min.  
MICROORGANISM: Kp  
Light Level: 2000 fc  
Nonwoven-1815-95-(1&2) uses Fort Howard X-173  
Nonwoven-1815-95-(3&4) uses Merfin 60850

| RUN # | Time '0' LOG # | DARK LOG # | LIGHT LOG # | LIGHT % KILL | COMMENTS |
|---|---|---|---|---|---|
|   |   |   |   |   | *Klebsiella pneumoniae*-- Seed = 5.5 |
| 1 | 5.5 | 5.4 | 5.5 | No Kill | No TBO |
| 2 | 5.5 | 5.5 | 2.9 | 99.7488 | Toluidine Blue O = 19 ppm Total |
| 3 | 5.5 | 5.5 | 5.5 | No Kill | No TBO |
| 4 | 5.5 | 5.6 | 3.9 | 97.4881 | Toluidine Blue O = 19 ppm Total |

TABLE 42

REFERENCE NO.: E 1815-95-(1–4) WRC 16502-(22 to 36)

DYE: TBO  
LIGHT EXPOSURE TIME: 60 min.  
MICROORGANISM: St  
Light Level: 2000 fc  
Nonwoven-1815-95-(1&2) uses Fort Howard X-173  
Nonwoven-1815-95-(3&4) uses Merfin 60850

| RUN # | Time '0' LOG # | DARK LOG # | LIGHT LOG # | LIGHT % KILL | COMMENTS |
|---|---|---|---|---|---|
|   |   |   |   |   | *Salmonella typhimurium*--Seed = 6.1 |
| 1 | 6.1 | 6.1 | 6.0 | 20.5672 | No TBO |
| 2 | 6.1 | 6.1 | 4.1 | 99.0000 | Toluidine Blue O = 19 ppm Total |
| 3 | 6.1 | 6.0 | 6.1 | No Kill | No TBO |
| 4 | 6.1 | 6.1 | 4.6 | 96.8377 | Toluidine Blue O = 19 ppm Total |

TABLE 43

REFERENCE NO.: E 1815-95-(1–4) WRC 16502-(22 to 36)

DYE: TBO  
LIGHT EXPOSURE TIME: 60 min.  
MICROORGANISM: Se  
Light Level: 2000 fc  
Nonwoven-1815-95-(1&2) uses Fort Howard X-173  
Nonwoven-1815-95-(3&4) uses Merfin 60850

| RUN # | Time '0' LOG # | DARK LOG # | LIGHT LOG # | LIGHT % KILL | COMMENTS |
|---|---|---|---|---|---|
|   |   |   |   |   | *Staphylococcus epidermidis*--Seed = 5.4 |
| 1 | 5.4 | 5.3 |   | 5.3 | 20.5672 No TBO |
| 2 | 5.4 | 5.3 | < 1.0 | > 99.9960 | Toluidine Blue O = 19 ppm Total |
| 3 | 5.4 | 5.4 |   | 5.3 | 20.5672 No TBO |
| 4 | 5.3 | 5.3 | ~ 1.2 | ~ 99.9921 | Toluidine Blue O = 19 ppm Total |

TABLE 44

REFERENCE NO.: E 1815-95-(1–4) WRC 16502-(22 to 36)

DYE: TBO  
LIGHT EXPOSURE TIME: 60 min.  
MICROORGANISM: Sm  
Light Level: 2000 fc  
Nonwoven-1815-95-(1&2) uses Fort Howard X-173  
Nonwoven-1815-95-(3&4) uses Merfin 60850

| RUN # | Time '0' LOG # | DARK LOG # | LIGHT LOG # | LIGHT % KILL | COMMENTS |
|---|---|---|---|---|---|
|   |   |   |   |   | *Serratia marcescens*-- Seed = 5.4 |
| 1 | 5.5 | 5.4 | 5.4 | 20.5672 | No TBO |
| 2 | 5.5 | 5.4 | 3.8 | 98.0047 | Toluidine Blue O = 19 ppm Total |
| 3 | 5.4 | 5.4 | 5.4 | No Kill | No TBO |
| 4 | 5.4 | 5.3 | 3.5 | 98.7411 | Toluidine Blue O = 19 ppm Total |

TABLE 45

REFERENCE NO.: E 1815-95-(1–4) WRC 16502-(22 to 36)

DYE: TBO  
LIGHT EXPOSURE TIME: 60 min.  
MICROORGANISM: Pv  
Light Level: 2000 fc  
Nonwoven-1815-95-(1&2) uses Fort Howard X-173  
Nonwoven-1815-95-(3&4) uses Merfin 60850

| RUN # | Time '0' LOG # | DARK LOG # | LIGHT LOG # | LIGHT % KILL | COMMENTS |
|---|---|---|---|---|---|
|   |   |   |   |   | *Proteus vulgaris*-- Seed = 5.9 |
| 1 | 5.8 | 5.8 | 5.7 | 20.5672 | No TBO |
| 2 | 5.7 | 5.7 | ~ 1.2 | 99.9968 | Toluidine Blue O = 19 ppm Total |
| 3 | 5.8 | 5.8 | 5.7 | 20.5672 | No TBO |
| 4 | 5.8 | 5.8 | ~ 1.0 | 99.9984 | Toluidine Blue O = 19 ppm Total |

TABLE 46

EXPERIMENT No. 3046-77-1

SUBSTRATE: 3046-76 (Buffered J80)  
BASIS WEIGHT-GSM: 85

| INGREDIENT | WET AMOUNT | SOLIDS % | WET % | DRY WEIGHT | DRY % |
|---|---|---|---|---|---|
| DI WAT | 6,894.6000 |  | 98.4943 |  |  |
| WB4000 | 11.6000 | 39.5000 | 0.1657 | 4.5820 | 97.9939 |
| TBO | 93.8000 | 0.1000 | 1.3400 | 0.0938 | 2.0061 |
| TOTAL: | 7,000.0000 | 0.0668 ACTUAL % SOLIDS | 100.0000 | 4.6758 | 100.0000 |

TABLE 47

EXPERIMENT No. 3046-77-2

SUBSTRATE: 3046-76 (Buffered J80)
BASIS WEIGHT-GSM: 85

| INGRE-DIENT | WET AMOUNT | SOLIDS % | WET % | DRY WEIGHT | DRY % |
|---|---|---|---|---|---|
| DI WAT | 6,874.7000 | | 98.2100 | | |
| WB4000 | 11.6000 | 39.5000 | 0.1657 | 4.5820 | 97.7680 |
| ROSE BENGAL | 113.7000 | 0.0920 | 1.6243 | 0.1046 | 2.2320 |
| TOTAL: | 7,000.0000 | 0.0670 ACTUAL % SOLIDS | 100.0000 | 4.6866 | 100.0000 |

TABLE 48

| | % COMPOSITION by WEIGHT | | | | |
|---|---|---|---|---|---|
| Experiment No. | Nonwoven J80B | Dye Binder WB4000 | Dyes/Antimicrobials TBO | Dyes/Antimicrobials RB | Dye/Binder Ratio |
| 3046-77-1 | 99.8999 | 0.0981 | 0.0020 | | 0.0204 |
| 3046-77-2 | 99.8997 | 0.0981 | | 0.0022 | 0.0224 |

TABLE 49

REF. NO.: 3046-77-(1,2): 3046-76  Virucidal Studies
DYE: TBO, RB  Date: September 17, 1993
EXPOSURE: 6, 20, & 60 min.  Light Level: 2000 fc
MICROBE: HIV-1 Free Virus in Phosphate buffered saline  Substrate - 3046-76 (Buffer and Wash Walkisoft J-80)

| Sample ID | Dark - 6 min. % KILL | Dark - 20 min. % KILL | Dark - 60 min. % KILL | Light - 6 min. % KILL | Light - 20 min. % KILL | Light - 60 min. % KILL | COMMENTS |
|---|---|---|---|---|---|---|---|
| | | | | | | 3.0 | Virus Titer |
| 3046-76 | No Kill | 80.0474 | 90.0000 | 49.8813 | 68.3772 | 98.0047 | J-80B(Washed) |
| 3046-77-1 | No Kill | 80.0474 | 90.0000 | 99.6838 | 99.6838 | 99.6838 | J-80B/WB4000/TBO 20 ppm |
| 3046-77-2 | No Kill | 80.0474 | 90.0000 | 99.0000 | 99.6838 | 99.6838 | J-80B/WB4000/RB 22 ppm |

TABLE 50

REFERENCE NO.: E 3046-77-1,2 WRC 17450-(58–59)

DYE: RB & TBO
LIGHT EXPOSURE TIME: 60 min.
MICROORGANISM: MRSA; Kp
Light Level: 2000 fc
Substrate-Walkisoft J80 Buffered and Washed

| RUN # | Time '0' LOG # | DARK LOG # | LIGHT LOG # | LIGHT % KILL | COMMENTS |
|---|---|---|---|---|---|
| | | | | | Methicillin Resistant *Staphylococcus aureus*--Seed = 4.3 |
| Control | 4.3 | 4.2 | 4.2 | 20.5672 | Walkisoft J80 Buffered and Washed |
| 1 | 4.3 | 4.3 | ~ 1.0 ~ | 99.9499 | Washed J80 Treated with Binder & TBO; 20 ppm |
| 2 | 4.3 | 4.3 | ~ 1.0 ~ | 99.9499 | Washed J80 Treated with Binder & RB; 22 ppm |
| Control | 4.3 | 4.2 | 4.2 | 20.5672 | Walkisoft J80 Raw Untreated Nonwoven |
| Beads | 4.4 | 4.3 | 3.7 | 80.0474 | 60 mg of Rose Bengal bound to resin beads |
| | | | | | *Klebsiella pneumoniae*--Seed = 5.2 |
| Control | 5.1 | 5.1 | 5.2 | No Kill | Walkisoft J80 Buffered and Washed |
| 1 | 5.1 | 5.1 | 4.3 | 54.1511 | Washed J80 Treated with Binder & TBO; 20 ppm |
| 2 | 5.2 | 5.1 | 5.2 | No Kill | Washed J80 Treated with Binder & RB; 22 ppm |
| Control | 5.1 | 5.1 | 5.1 | No Kill | Walkisoft J80 Raw Untreated Nonwoven |

TABLE 51

REFERENCE NO.: 3046-77-(1,2)

DYE: TBO, RB
EXPOSURE TIME: 20, & 60 min.
MICROORGANISM: HIV-1 Free Virus
Date: November 23, 1993
Light Level: 2000 fc
Substrate—J80B; 3046-76 (Buffer and Wash Walkisoft J-80)

| Sample ID | Dark-20 min. % KILL | Dark-60 min. % KILL | Light-20 min. % KILL | Light-60 min. % KILL | COMMENTS |
|---|---|---|---|---|---|
| | | | | | Virus Titer in PBS (phosphate buffered saline) = 4.3 |
| 3046-76 | 99.7812 | 99.9852 | 99.9532 | 99.9852 | J-80B(Washed) |
| 3046-77-1 | 99.7812 | 99.9852 | 99.9852 | 99.9852 | J-80B/WB4000/TBO 20 ppm |
| 3046-77-2 | 99.7812 | 99.9852 | 99.9852 | 99.9852 | J-80B/WB4000/RB 22 ppm |
| | | | | | Virus Titer in Whole Human Blood = 4.0 |
| 3046-76 | No Kill | 90.0000 | 68.3772 | 78.6204 | J-80B(Washed) |
| 3046-77-1 | 53.2265 | 53.2265 | 96.8377 | 99.9684 | J-80B/WB4000/TBO 20 ppm |
| 3046-77-2 | 53.2265 | 90.0000 | 78.6204 | 90.0000 | J-80B/WB4000/RB 22 ppm |

TABLE 52

EXPERIMENT No. 3057-30-1A

SUBSTRATE: WA-2(Lot # 1942)
BASIS WEIGHT-GSM: 85

| INGREDIENT | WET AMOUNT | SOLIDS % | WET % | DRY WEIGHT | DRY % |
|---|---|---|---|---|---|
| DI WAT | 598.7000 | | 85.5286 | | |
| TBO | 9.4000 | 0.1000 | 1.3429 | 0.0094 | 2.0047 |
| VISCARIN SD 389 | 91.9000 | 0.5000 | 13.1286 | 0.4595 | 97.9953 |
| TOTAL: | 700.0000 | 0.0670 ACTUAL % SOLIDS | 100.0000 | 0.4689 | 100.0000 |

TABLE 53

EXPERIMENT No. 3057-30-1B

SUBSTRATE: WA-2(Lot # 1942)
BASIS WEIGHT-GSM: 85

| INGREDIENT | WET AMOUNT | SOLIDS % | WET % | DRY WEIGHT | DRY % |
|---|---|---|---|---|---|
| DI WAT | 589.3000 | | 84.1857 | | |
| TBO | 18.8000 | 0.1000 | 2.6857 | 0.0188 | 3.9306 |
| VISCARIN SD 389 | 91.9000 | 0.5000 | 13.1286 | 0.4595 | 96.0694 |
| TOTAL: | 700.0000 | 0.0683 ACTUAL % SOLIDS | 100.0000 | 0.4783 | 100.0000 |

TABLE 54

EXPERIMENT No. 3057-30-1C

SUBSTRATE: WA-2(Lot # 1942)
BASIS WEIGHT-GSM: 85

| INGREDIENT | WET AMOUNT | SOLIDS % | WET % | DRY WEIGHT | DRY % |
|---|---|---|---|---|---|
| DI WAT | 497.4000 | | 71.0571 | | |
| TBO | 18.8000 | 0.1000 | 2.6857 | 0.0188 | 2.0047 |
| VISCARIN SD 389 | 183.8000 | 0.5000 | 26.2571 | 0.9190 | 97.9953 |
| TOTAL: | 700.0000 | 0.1340 ACTUAL % SOLIDS | 100.0000 | 0.9378 | 100.0000 |

TABLE 55

EXPERIMENT No. 3057-30-1D

SUBSTRATE: WA-2(Lot # 1942)
BASIS WEIGHT-GSM: 85

| INGREDIENT | WET AMOUNT | SOLIDS % | WET % | DRY WEIGHT | DRY % |
|---|---|---|---|---|---|
| DI WAT | 478.6000 | | 68.3714 | | |
| TBO | 37.6000 | 0.1000 | 5.3714 | 0.0376 | 3.9306 |
| VISCARIN SD 389 | 183.8000 | 0.5000 | 26.2571 | 0.9190 | 96.0694 |
| TOTAL: | 700.0000 | 0.1367 ACTUAL % SOLIDS | 100.0000 | 0.9566 | 100.0000 |

TABLE 56

EXPERIMENT No. 3057-30-2A

SUBSTRATE: WA-2(Lot # 1942)
BASIS WEIGHT-GSM: 85

| INGREDIENT | WET AMOUNT | SOLIDS % | WET % | DRY WEIGHT | DRY % |
|---|---|---|---|---|---|
| DI WAT | 597.8000 | | 85.4000 | | |
| THIONIN | 10.3000 | 0.0910 | 1.4714 | 0.0094 | 1.9990 |
| VISCARIN SD 389 | 91.9000 | 0.5000 | 13.1286 | 0.4595 | 98.0010 |
| TOTAL: | 700.0000 | 0.0670 ACTUAL % SOLIDS | 100.0000 | 0.4689 | 100.0000 |

TABLE 57

EXPERIMENT No. 3057-30-3A

SUBSTRATE: WA-2(Lot # 1942)
BASIS WEIGHT-GSM: 85

| INGREDIENT | WET AMOUNT | SOLIDS % | WET % | DRY WEIGHT | DRY % |
|---|---|---|---|---|---|
| DI WAT | 596.7000 | | 85.2429 | | |
| METHYLENE BLUE | 11.4000 | 0.0820 | 1.6286 | 0.0093 | 1.9938 |

TABLE 57-continued

EXPERIMENT No. 3057-30-3A

SUBSTRATE: WA-2(Lot # 1942)
BASIS WEIGHT-GSM: 85

| INGRE-DIENT | WET AMOUNT | SOLIDS % | WET % | DRY WEIGHT | DRY % |
|---|---|---|---|---|---|
| VISCARIN SD 389 | 91.9000 | 0.5000 | 13.1286 | 0.4595 | 98.0062 |
| TOTAL: | 700.0000 | 0.0670 ACTUAL % SOLIDS | 100.0000 | 0.4688 | 100.0000 |

TABLE 58

EXPERIMENT No. 3057-30-3B

SUBSTRATE: WA-2(Lot # 1942)
BASIS WEIGHT-GSM: 85

| INGRE-DIENT | WET AMOUNT | SOLIDS % | WET % | DRY WEIGHT | DRY % |
|---|---|---|---|---|---|
| DI WAT | 585.2000 | | 83.6000 | | |
| METHYL-ENE BLUE | 22.9000 | 0.0820 | 3.2714 | 0.0188 | 3.9262 |
| VISCARIN SD 389 | 91.9000 | 0.5000 | 13.1286 | 0.4595 | 96.0738 |
| TOTAL: | 700.0000 | 0.0683 ACTUAL % SOLIDS | 100.0000 | 0.4783 | 100.0000 |

TABLE 59

EXPERIMENT No. 3057-30-3C

SUBSTRATE: WA-2(Lot # 1942)
BASIS WEIGHT-GSM: 85

| INGRE-DIENT | WET AMOUNT | SOLIDS % | WET % | DRY WEIGHT | DRY % |
|---|---|---|---|---|---|
| DI WAT | 493.4000 | | 70.4857 | | |
| METHYL-ENE BLUE | 22.8000 | 0.0820 | 3.2571 | 0.0187 | 1.9938 |
| VISCARIN SD 389 | 183.8000 | 0.5000 | 26.2571 | 0.9190 | 98.0062 |
| TOTAL: | 700.0000 | 0.1340 ACTUAL % SOLIDS | 100.0000 | 0.9377 | 100.0000 |

TABLE 60

EXPERIMENT No. 3057-30-3D

SUBSTRATE: WA-2(Lot # 1942)
BASIS WEIGHT-GSM: 85

| INGRE-DIENT | WET AMOUNT | SOLIDS % | WET % | DRY WEIGHT | DRY % |
|---|---|---|---|---|---|
| DI WAT | 470.4000 | | 67.2000 | | |
| METHYL-ENE BLUE | 45.8000 | 0.0820 | 6.5429 | 0.0376 | 3.9262 |
| VISCARIN SD 389 | 183.8000 | 0.5000 | 26.2571 | 0.9190 | 96.0738 |
| TOTAL: | 700.0000 | 0.1367 ACTUAL % SOLIDS | 100.0000 | 0.9566 | 100.0000 |

TABLE 61

EXPERIMENT No. 3057-30-4

SUBSTRATE: WA-2(Lot # 1942)
BASIS WEIGHT-GSM: 85

| INGRE-DIENT | WET AMOUNT | SOLIDS % | WET % | DRY WEIGHT | DRY % |
|---|---|---|---|---|---|
| DI WAT | 608.1000 | | 86.8714 | | |
| VISCARIN SD 389 | 91.9000 | 0.5000 | 13.1286 | 0.4595 | 100.0000 |
| TOTAL: | 700.0000 | 0.0656 ACTUAL % SOLIDS | 100.0000 | 0.4595 | 100.0000 |

TABLE 62

EXPERIMENT No. 3057-34-1

SUBSTRATE: WA-2(Lot # 1942)
BASIS WEIGHT-GSM: 85

| INGRE-DIENT | WET AMOUNT | SOLIDS % | WET % | DRY WEIGHT | DRY % |
|---|---|---|---|---|---|
| DI WAT | 577.0000 | | 82.4286 | | |
| TBO | 9.4000 | 0.1000 | 1.3429 | 0.0094 | 1.9277 |
| METHYL-ENE BLUE | 11.4000 | 0.0820 | 1.6286 | 0.0093 | 1.9171 |
| THIONIN | 10.3000 | 0.0910 | 1.4714 | 0.0094 | 1.9222 |
| VISCARIN SD 389 | 91.9000 | 0.5000 | 13.1286 | 0.4595 | 94.2330 |
| TOTAL: | 700.0000 | 0.0697 ACTUAL % SOLIDS | 100.0000 | 0.4876 | 100.0000 |

TABLE 63

% COMPOSITION by WEIGHT

| | Nonwoven | Dye Binder | Dyes/Antimicrobials | | | Dye/Binder |
|---|---|---|---|---|---|---|
| Experiment No. | WA-2 | VIS389 | TBO | TH | MB | Ratio |
| 3057-30-1A | 99.8996 | 0.0984 | 0.0020 | | | 0.0203 |
| 3057-30-1B | 99.8976 | 0.0984 | 0.0040 | | | 0.0407 |
| 3057-30-1C | 99.7995 | 0.1965 | 0.0040 | | | 0.0204 |
| 3057-30-1D | 99.7955 | 0.1965 | 0.0080 | | | 0.0407 |
| 3057-30-2A | 99.8996 | 0.0984 | | 0.0020 | | 0.0203 |
| 3057-30-3A | 99.8998 | 0.0984 | | | 0.0018 | 0.0183 |
| 3057-30-3B | 99.8976 | 0.0984 | | | 0.0040 | 0.0407 |
| 3057-30-3C | 99.7995 | 0.1965 | | | 0.0040 | 0.0204 |
| 3057-30-3D | 99.7954 | 0.1965 | | | 0.0080 | 0.0409 |
| 3057-30-4 | 99.9016 | 0.0984 | | | | |
| 3057-34-1 | 99.8956 | 0.0984 | 0.0020 | 0.0020 | 0.0020 | 0.0610 |

TABLE 64

REFERENCE NO.: 3057-30 Series  Endura Laboratory Testing
DYES: TBO, MB, TH  Date: February 17, 1994
Binder: Carrageenan  Substrate-Walkisoft WA-2

| SAMPLE ID | CROCKING AATCC 8-1989 Grade Target/Minimum 3.8/2.3 | LEACHING 1 G SAMPLE/ 50 G DI WATER Observation None/Very Slight | COMMENTS |
|---|---|---|---|
| 3057-30-1A | 4.5 | — | WA-2/Viscarin/TBO at 20 ppm |
| 3057-30-1B | 4.5 | — | WA-2/Viscarin/TBO at 40 ppm |
| 3057-30-1C | 4.5 | — | WA-2/Viscarin at 2x/TBO at 40 ppm |
| 3057-30-1D | 4.0 | None | WA-2/Viscarin at 2x/TBO at 80 ppm |
| 3057-30-2A | 3.5 | — | WA-2/Viscarin/TH at 20 ppm; Bath Unstable |
| 3057-30-3A | 4.5 | — | WA-2/Viscarin/MB at 18 ppm |
| 3057-30-3B | 4.5 | — | WA-2/Viscarin/MB at 40 ppm |
| 3057-30-3C | 4.5 | — | WA-2/Viscarin at 2x/MB at 40 ppm |
| 3057-30-3D | 3.5 | None | WA-2/Viscarin at 2x/MB at 66 ppm |
| 3057-34-1 | — | — | WA-2/Viscarin/TBO, TH, MB at 20 ppm each |
| 3057-30-4 | — | — | WA-2/Viscarin Control |

TABLE 65

REFERENCE NO.: SRI Virucidal Studies
DYES: TBO, MB, TH  Appendix 3, Support Documents, G
LIGHT EXPOSURE TIME: 15 min.  Date: March 16, 1994
MICROORGANISM: HIV-1 suspended in  Light Level: 2000 fc
Whole Human Blood  Substrate - Walkisoft WA-2

| SAMPLE ID | 15 Minutes LIGHT LOG # | | 15 Minutes LIGHT % KILL | COMMENTS |
|---|---|---|---|---|
| | 3.5 | | | Virus Titer |
| 3057-30-1A | 1.0 | | 99.6838 | WA-2/Viscarin/TBO at 20 ppm |
| 3057-30-1D | 0.5 | ~ | 99.9000 | WA-2/Viscarin/TBO at 80 ppm |
| 3057-30-2A | 0.5 | ~ | 99.9000 | WA-2/Viscarin/TH at 20 ppm |
| 3057-30-3A | 0.5 | | 99.9000 | WA-2/Viscarin/MB at 18 ppm |
| 3057-30-3D | 0.5 | ~ | 99.9000 | WA-2/Viscarin/MB at 66 ppm |
| 3057-34-1 | 0.5 | ~ | 99.9000 | WA-2/Viscarin/TBO, TH, MB all at 20 ppm |
| 3057-30-4 | 3.7 | | No Kill | WA-2/Viscarin Control |
| | Zero Time Control | | | |
| 3057-30-4 | 4.2 | | No Kill | WA-2/Viscarin (Zero Time) Control |

TABLE 66

REFERENCE NO.: SRI Virucidal Studies
DYES: TBO, MB, TH
LIGHT EXPOSURE TIME: 120 min.
MICROORGANISM: H9 Cells Chronically Infected with HIV-1 in Whole Human Blood Appendix 3, Support Documents, J
Date: June 28, 1994
Light Level: 2000 fc
Substrate-Walkisoft WA-2

| SAMPLE ID | 120 Minutes LIGHT LOG # | 120 Minutes LIGHT % KILL | COMMENTS |
|---|---|---|---|
|  | 3.7 |  | Virus Titer |
| 3057-30-1A | 2.7 | 90.0000 | WA-2/Viscarin/TBO at 20 ppm |
| 3057-30-1D | 1.3 | 99.6019 | WA-2/Viscarin/TBO at 80 ppm |
| 3057-30-2A | 1.7 | 99.0000 | WA-2/Viscarin/TH at 20 ppm |
| 3057-30-3A | 1.5 | 99.3690 | WA-2/Viscarin/MB at 18 ppm |
| 3057-30-3D | 0.5 | ~ 99.9369 | WA-2/Viscarin/MB at 66 ppm |
| 3057-34-1 | 1.7 | 99.0000 | WA-2/Viscarin/TBO, TH, MB all at 20 ppm |
| 3057-30-4 | 3.0 | 80.0474 | WA-2/Viscarin Control |
|  | Zero Time Control |  |  |
| 3057-30-4 | 3.5 | 36.9043 | WA-2/Viscarin (Zero Time) Control |

What is claimed is:

1. A substrate selected from the group consisting of a nonwoven material and a woven material, said substrate comprising a binder and a light-activatable anionic or cationic dye capable of generating singlet oxygen in the presence of oxygen and upon exposure to light as an antimicrobial or antiviral agent, said anionic or cationic dye being bound to said substrate by said binder in an amount effective for rendering said substrate antimicrobial or antiviral upon exposure of said substrate to light, wherein said binder is carrageenan.

2. The substrate of claim 1, wherein said binder is a cationic or anionic water soluble polymer.

3. The substrate of claim 2, wherein said water soluble polymer is a blocked waterborne polyurethane prepolymer.

4. The substrate of claim 1, wherein said dye is selected from the group consisting of Toluidine Blue O, Thionin, Methylene Blue and Rose Bengal.

5. The substrate of claim 1, wherein said nonwoven material comprises cellulose fiber.

6. The substrate of claim 1, wherein said nonwoven material is in the form of a surgical drape.

7. A substrate selected from the group consisting of paper, a nonwoven material, a woven material, and a polymeric film, said substrate comprising a binder and an anionic or cationic dye capable of generating singlet oxygen in the presence of oxygen and upon exposure to light as an antiviral agent, said anionic or cationic dye being bound to said substrate by said binder in an amount effective for rendering said substrate antiviral, said dye exhibiting antiviral properties upon activation by light, wherein said binder is carrageenan.

8. The substrate of claim 7, wherein said binder is a cationic or anionic water soluble polymer.

9. The substrate of claim 8, wherein said water soluble polymer is a blocked waterborne polyurethane prepolymer.

10. The substrate of claim 7, wherein said dye is selected from the group consisting of Toluidine Blue O, Thionin, Methylene Blue and Rose Bengal.

11. The substrate of claim 7, wherein said nonwoven material comprises cellulose fiber.

12. The substrate of claim 7, wherein said nonwoven material is in the form of a surgical drape.

* * * * *